US010271863B2

(12) United States Patent
Marks et al.

(10) Patent No.: US 10,271,863 B2
(45) Date of Patent: Apr. 30, 2019

(54) INTRAVASCULAR THROMBOEMBOLECTOMY DEVICE COMPRISING A PLURALITY OF CLOT ENGAGING ELEMENTS AND METHOD USING THE SAME

(71) Applicant: Likemark Medical Inc., Hillsborough, CA (US)

(72) Inventors: Michael P. Marks, Hillsborough, CA (US); Like Que, Livermore, CA (US)

(73) Assignee: ThrombX Medical, Inc., Hillsborough, CA (US)

( * ) Notice: Subject to any disclaimer, the term of this patent is extended or adjusted under 35 U.S.C. 154(b) by 797 days.

(21) Appl. No.: 14/638,994

(22) Filed: Mar. 4, 2015

(65) Prior Publication Data

US 2015/0250497 A1    Sep. 10, 2015

Related U.S. Application Data

(60) Provisional application No. 61/947,957, filed on Mar. 4, 2014.

(51) Int. Cl.
*A61B 17/221* (2006.01)

(52) U.S. Cl.
CPC .... *A61B 17/221* (2013.01); *A61B 2017/2212* (2013.01); *A61B 2017/2215* (2013.01)

(58) Field of Classification Search
CPC ...... A61F 2/013; A61F 2/01; A61F 2002/016; A61F 2002/011; A61F 2002/015; A61F 2002/018; A61B 17/22031; A61B 17/320725; A61B 17/221; A61B 2017/22034; A61B 2017/2212; A61B 2017/2215; A61B 17/3207;

(Continued)

(56) References Cited

U.S. PATENT DOCUMENTS

| | | | |
|---|---|---|---|
| 5,011,488 A | 4/1991 | Ginsburg | |
| 5,846,251 A | 12/1998 | Hart | |
| 5,972,019 A | 10/1999 | Engelson et al. | |

(Continued)

FOREIGN PATENT DOCUMENTS

| | | |
|---|---|---|
| CN | 102036611 A | 4/2011 |
| EP | 1 054 635 B1 | 1/2010 |

(Continued)

OTHER PUBLICATIONS

Extended European Search dated Jun. 17, 2017 in corresponding European Application 15758875.7, filed Aug. 26, 2016, in 9 pgs.

(Continued)

*Primary Examiner* — Eric J Rosen
*Assistant Examiner* — Chima U Igboko
(74) *Attorney, Agent, or Firm* — Knobbe, Martens, Olson & Bear, LLP

(57) ABSTRACT

A device and a method for increasing or restoring a flow in a body lumen are provided. The device and the method may treat conditions like a stroke by removing a clot from a blood vessel and/or reopen the vessel. The device may have a plurality of engaging elements, wires that can link at least two engaging elements, a central wire, and proximal control element. The positions of the engaging elements and the distance there between can be adjusted to ensure the engagement of the clot or occlusion.

17 Claims, 19 Drawing Sheets

(58) Field of Classification Search
CPC .... A61B 17/320758; A61B 17/320783; A61B 2017/32004

See application file for complete search history.

(56) References Cited

U.S. PATENT DOCUMENTS

| | | | |
|---|---|---|---|
| 5,984,957 | A | 11/1999 | Laptewicz, Jr. et al. |
| 6,096,053 | A | 8/2000 | Bates |
| 6,248,128 | B1 | 6/2001 | Berry et al. |
| 6,458,139 | B1 | 10/2002 | Palmer et al. |
| 7,029,488 | B2 | 4/2006 | Schonboltz et al. |
| 8,858,497 | B2 | 10/2014 | Di Palma et al. |
| 2002/0091407 | A1 | 7/2002 | Zadno-Azizi et al. |
| 2002/0123765 | A1 | 9/2002 | Sepetka |
| 2003/0163158 | A1 | 8/2003 | White |
| 2003/0176886 | A1 | 9/2003 | Wholey et al. |
| 2004/0260333 | A1 | 12/2004 | Dubrul |
| 2005/0113862 | A1 | 5/2005 | Besselink et al. |
| 2006/0155305 | A1 | 7/2006 | Freudenthal et al. |
| 2007/0100422 | A1 | 5/2007 | Shumer et al. |
| 2008/0097401 | A1 | 4/2008 | Trapp et al. |
| 2008/0114439 | A1 | 5/2008 | Ramaiah et al. |
| 2008/0262487 | A1 | 10/2008 | Wensel et al. |
| 2009/0054918 | A1 | 2/2009 | Henson |
| 2009/0105722 | A1 | 4/2009 | Fulkerson et al. |
| 2009/0105737 | A1 | 4/2009 | Fulkerson et al. |
| 2009/0192485 | A1 | 7/2009 | Heuser |
| 2009/0198269 | A1 | 8/2009 | Hannes et al. |
| 2009/0221967 | A1 | 9/2009 | Thommen et al. |
| 2009/0292297 | A1 | 11/2009 | Ferrere |
| 2009/0299393 | A1 | 12/2009 | Martin et al. |
| 2010/0004726 | A1 | 1/2010 | Hancock et al. |
| 2010/0114017 | A1 | 5/2010 | Lenker et al. |
| 2010/0268265 | A1 | 10/2010 | Krolik |
| 2011/0202088 | A1 | 8/2011 | Eckhouse et al. |
| 2012/0059356 | A1 | 3/2012 | Di Palma et al. |
| 2012/0165859 | A1 | 6/2012 | Eckhouse et al. |
| 2013/0030460 | A1 | 1/2013 | Marks et al. |
| 2013/0030461 | A1 | 1/2013 | Marks et al. |
| 2013/0345739 | A1* | 12/2013 | Brady .................. A61B 17/221 606/200 |
| 2014/0046359 | A1 | 2/2014 | Bowman et al. |
| 2014/0052161 | A1 | 2/2014 | Cully et al. |

FOREIGN PATENT DOCUMENTS

| | | |
|---|---|---|
| EP | 1 629 784 B1 | 1/2010 |
| EP | 1 667 588 B1 | 1/2010 |
| JP | 2003033359 A | 2/2003 |
| WO | 02/055146 A1 | 7/2002 |
| WO | 2007/004221 A1 | 1/2007 |
| WO | 2009/076482 A1 | 6/2009 |
| WO | 2011/006013 A1 | 1/2011 |

OTHER PUBLICATIONS

International Search Report and Written Opinion dated Jun. 2, 2015 for PCT/US2015/018752.
International Search Report dated Nov. 1, 2012 for international Application No. PCT/US2012/048158.
Extended European Search Report for EP 12 81 7411.
Office Action dated Jan. 23, 2015 for CN201280036998.X.
Restriction Requirement dated Feb. 4, 2013 for U.S. Appl. No. 13/191,306.
Office Action dated May 10, 2013 for U.S. Appl. No. 13/191,306.
Final Office Action dated Dec. 17, 2013 for U.S. Appl. No. 13/191,306.
Advisory Action dated May 5, 2014 for U.S. Appl. No. 13/191,306.
Office Action dated Aug. 26, 2014 for U.S. Appl. No. 13/191,306.
Final Office Action dated Jan. 27, 2015 for U.S. Appl. No. 13/191,306.
Restriction Requirement dated Jun. 21, 2013 for U.S. Appl. No. 13/543,657.
Office Action dated Aug. 30, 2012 for U.S. Appl. No. 13/543,657.
Final Office Action dated Feb. 11, 2014, for U.S. Appl. No. 13/543,657.
Office Action dated Aug. 21, 2014 for U.S. Appl. No. 13/543,657.
Final Office Action dated Jan. 15, 2015 for U.S. Appl. No. 13/543,657.
International Report on Patentability dated Nov. 21, 2013 for PCT/US2012/048158.
Decision of Rejection dated Sep. 27, 2016 in corresponding Chinese Application No. 201280036998.X, filed Jan. 24, 2014.
Office Action dated Aug. 27, 2015 for U.S. Appl. No. 13/191,306, filed Jul. 26, 2011, 21 pages.
Notice of Panel Decision from Pre-Appeal Brief Review dated Dec. 15, 2015 for U.S. Appl. No. 13/191,306, filed Jul. 26, 2011, 2 pages.
Notice of Abandonment dated Jul. 18, 2016 for U.S. Appl. No. 13/191,306, filed Jul. 26, 2011, 2 pages.
Office Action dated Sep. 18, 2015 for U.S. Appl. No. 13/543,657, filed Jul. 6, 2012, 21 pages.
Office Communication dated Jul. 1, 2016 for U.S. Appl. No. 13/543,657, filed Jul. 6, 2012, 2 pages.
Final Office Action dated Dec. 30, 2016 for U.S. Appl. No. 13/543,657, filed Jul. 6, 2012, 22 pages.
Office Action dated Jun. 2, 2017 for U.S. Appl. No. 13/543,657, filed Jul. 6, 2012, 15 pages.
Final Office Action dated Nov. 1, 2017 for U.S. Appl. No. 13/543,657, filed Jul. 6, 2012, 13 pages.
Advisory Action dated Jan. 25, 2018 for U.S. Appl. No. 13/543,657, filed Jul. 6, 2012, 3 pages.
Notice on Reexamination dated Sep. 18, 2017 for Chinese Application No. 201280036998.X filed Jan. 24, 2014, 12 pages.
Office Action dated Jan. 13, 2017 for U.S. Appl. No. 15/190,047, filed Jun. 22, 2016, 21 pages.
Final Office Action dated Jun. 5, 2017 for U.S. Appl. No. 15/190,047, filed Jun. 22, 2016, 12 pages.
Office Action dated Aug. 10, 2017 for U.S. Appl. No. 15/190,047, filed Jun. 22, 2016, 14 pages.
Final Office Action dated Dec. 15, 2017 for U.S. Appl. No. 15/190,047, filed Jun. 22, 2016, 15 pages.
Office Action dated Dec. 14, 2017 for European Application No. 12817411.7 filed Jan. 28, 2014, 4 pages.
Office Action dated Jun. 2, 2016 for Japanese Application No. 2014-522968 filed Jan. 6, 2014, 8 pages.
Notice of Allowance dated Sep. 20, 2016 for Japanese Application No. 2014-522968 filed Jan. 6, 2014, 3 pages.

\* cited by examiner

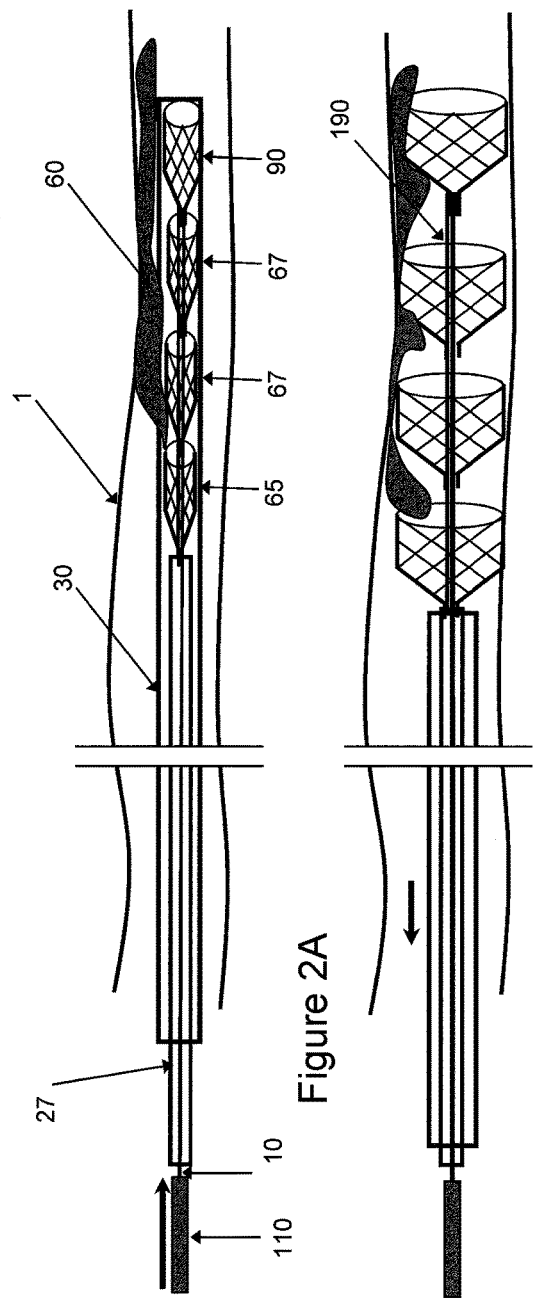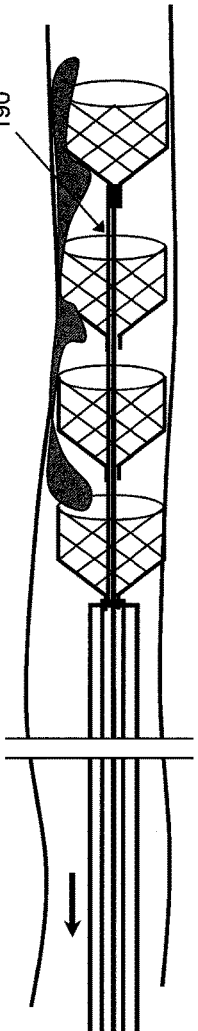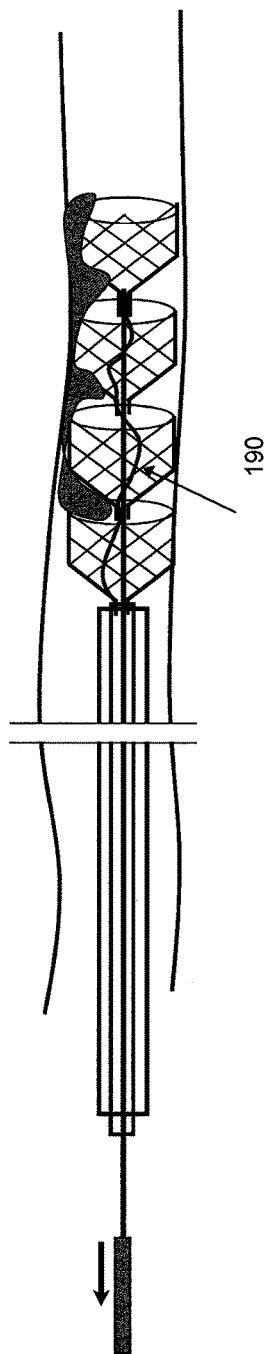
Figure 2A
Figure 2B
Figure 2C

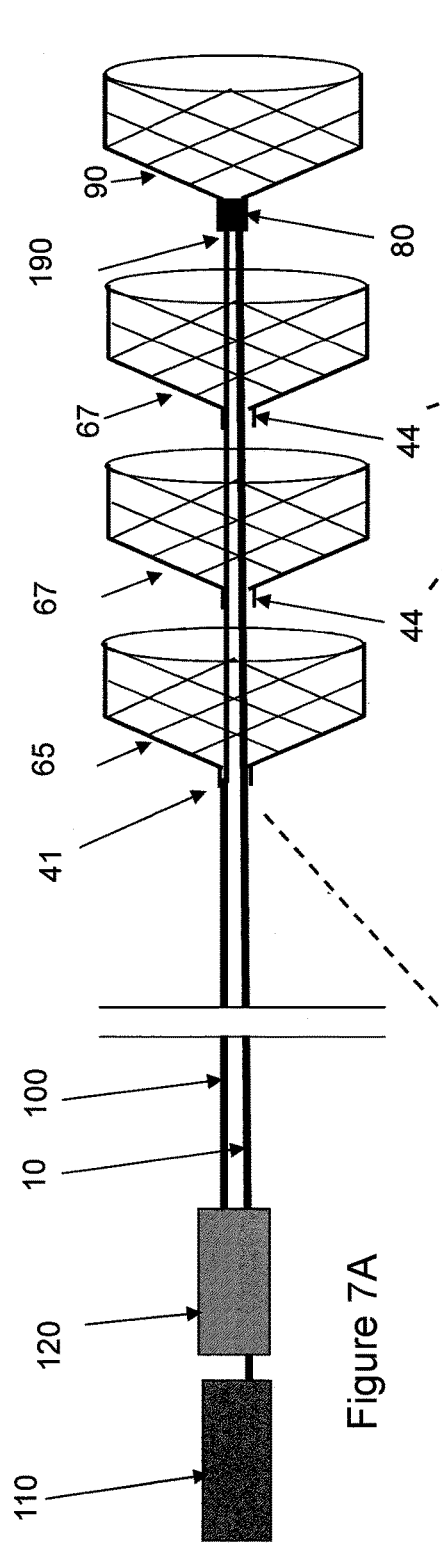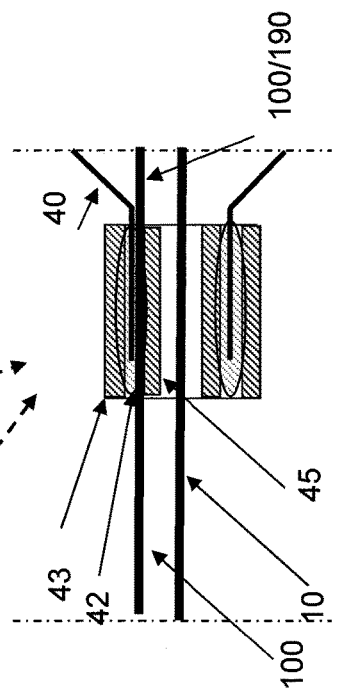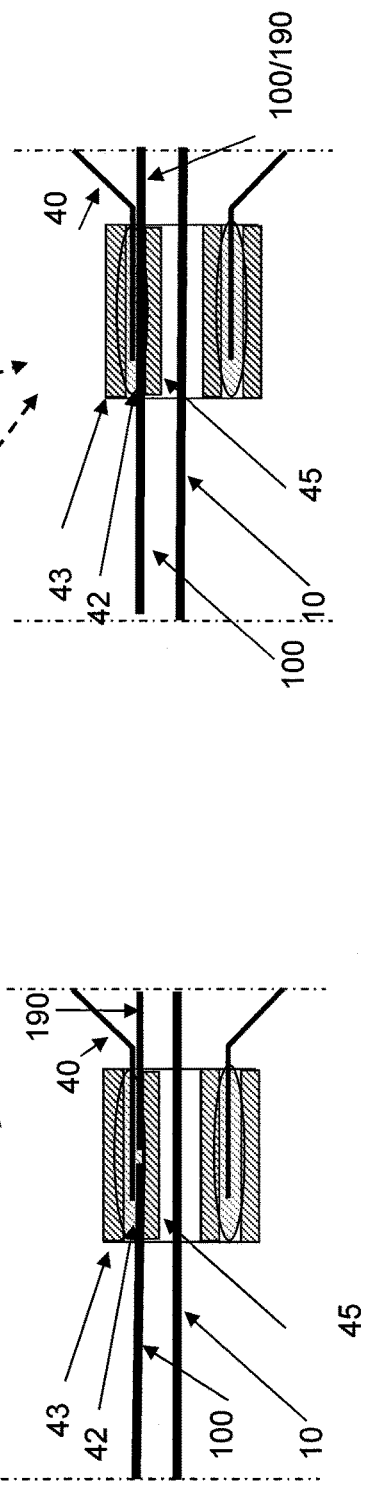

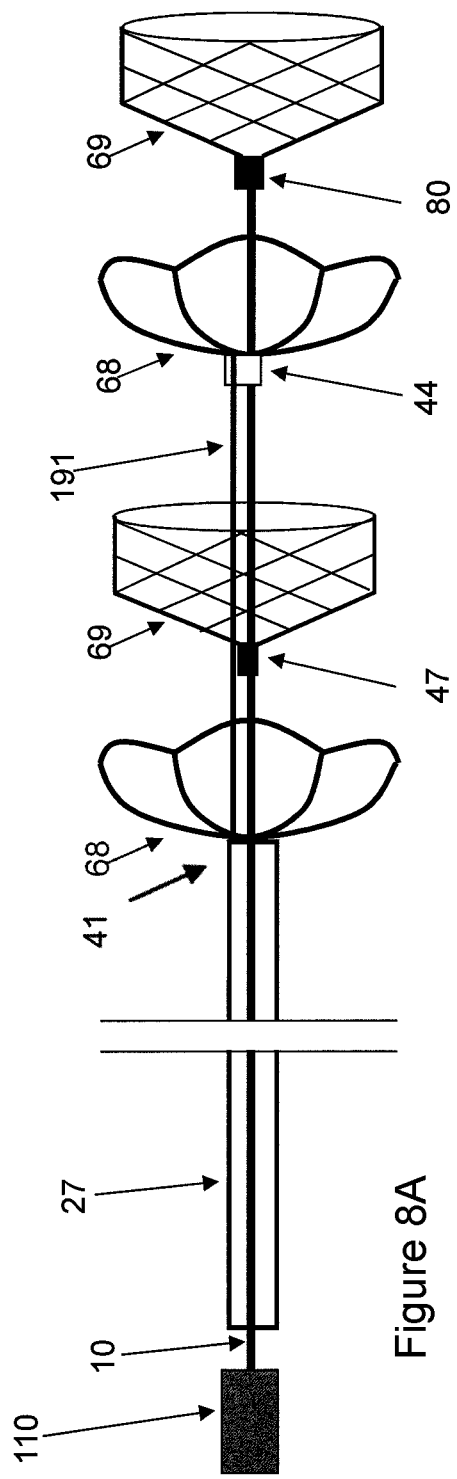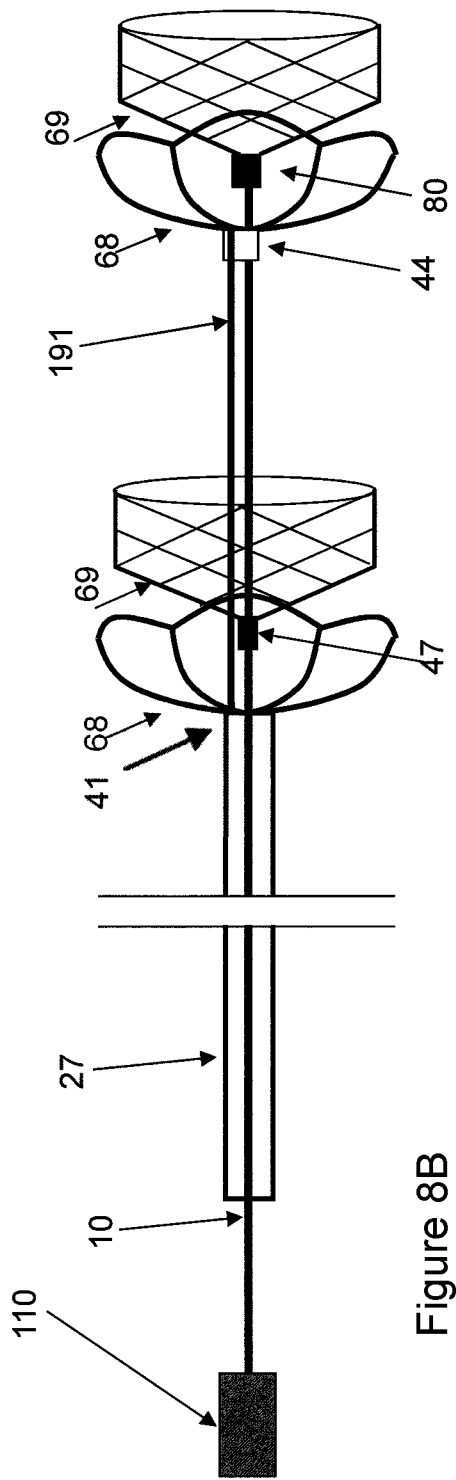
Figure 8A
Figure 8B

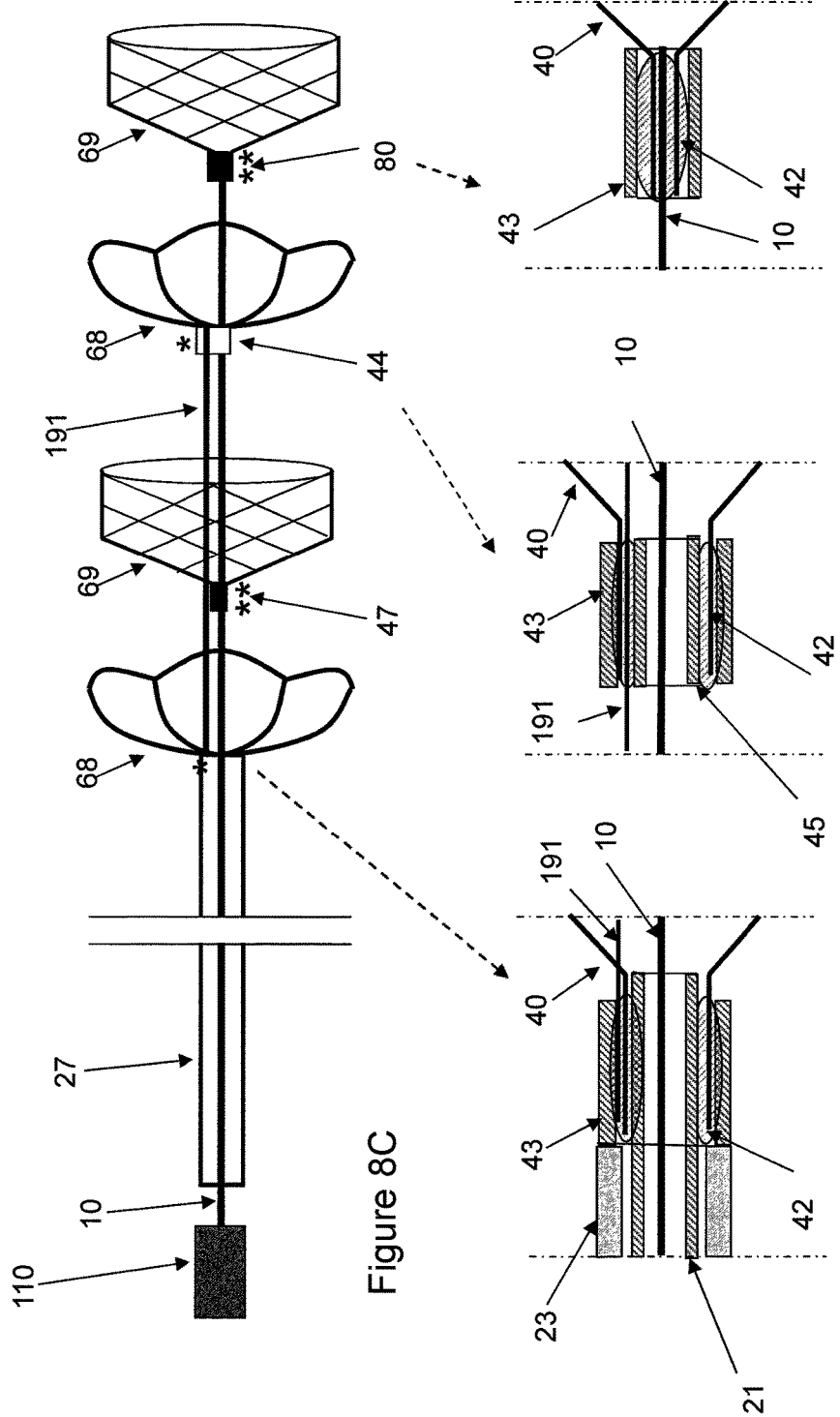

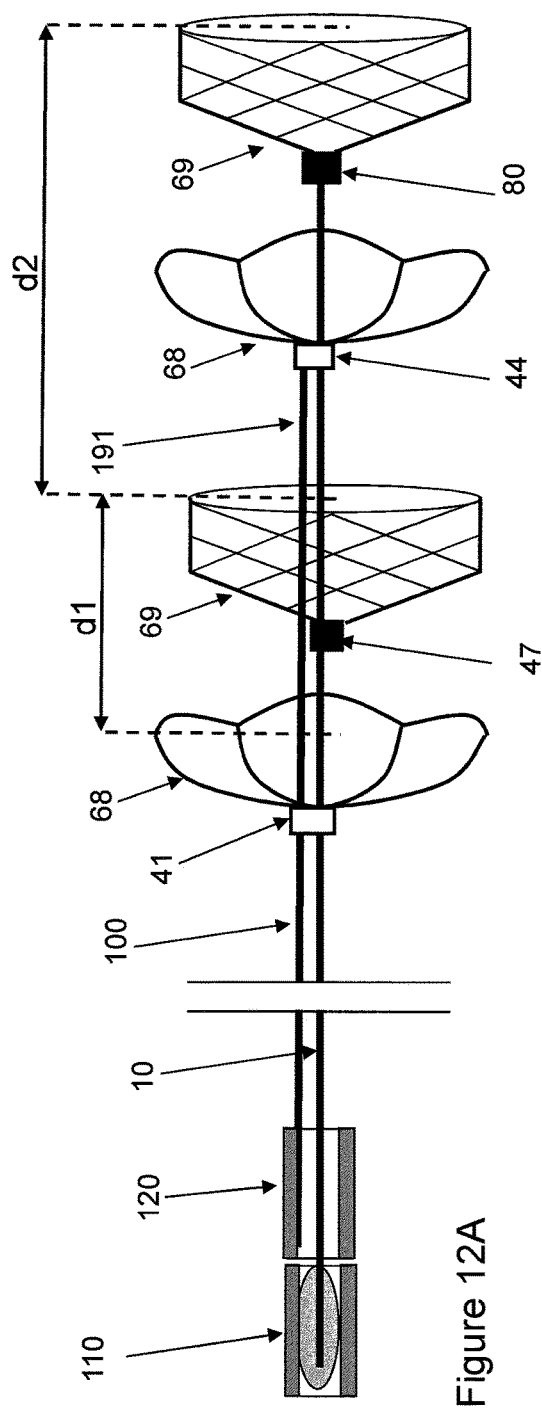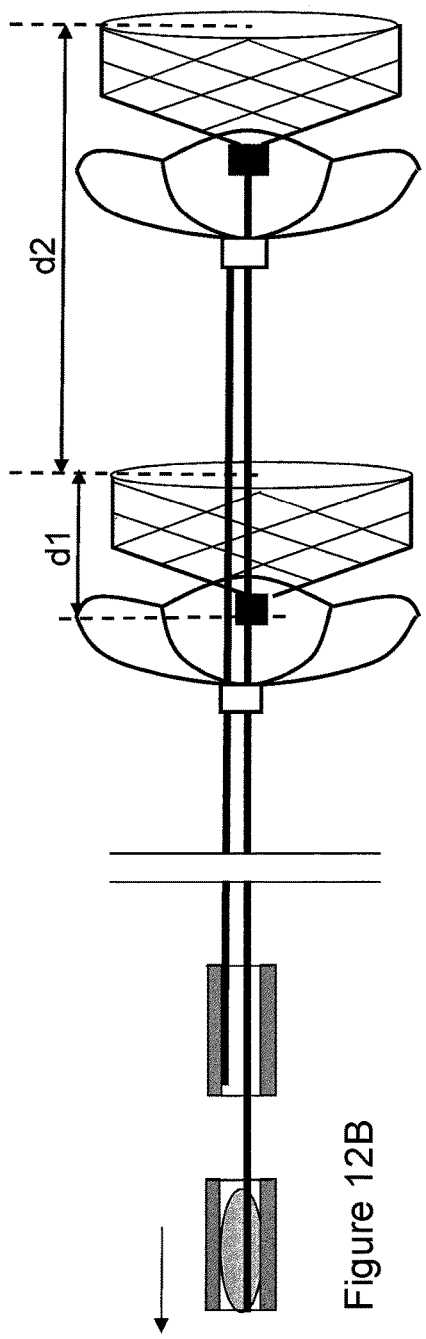
Figure 12A
Figure 12B

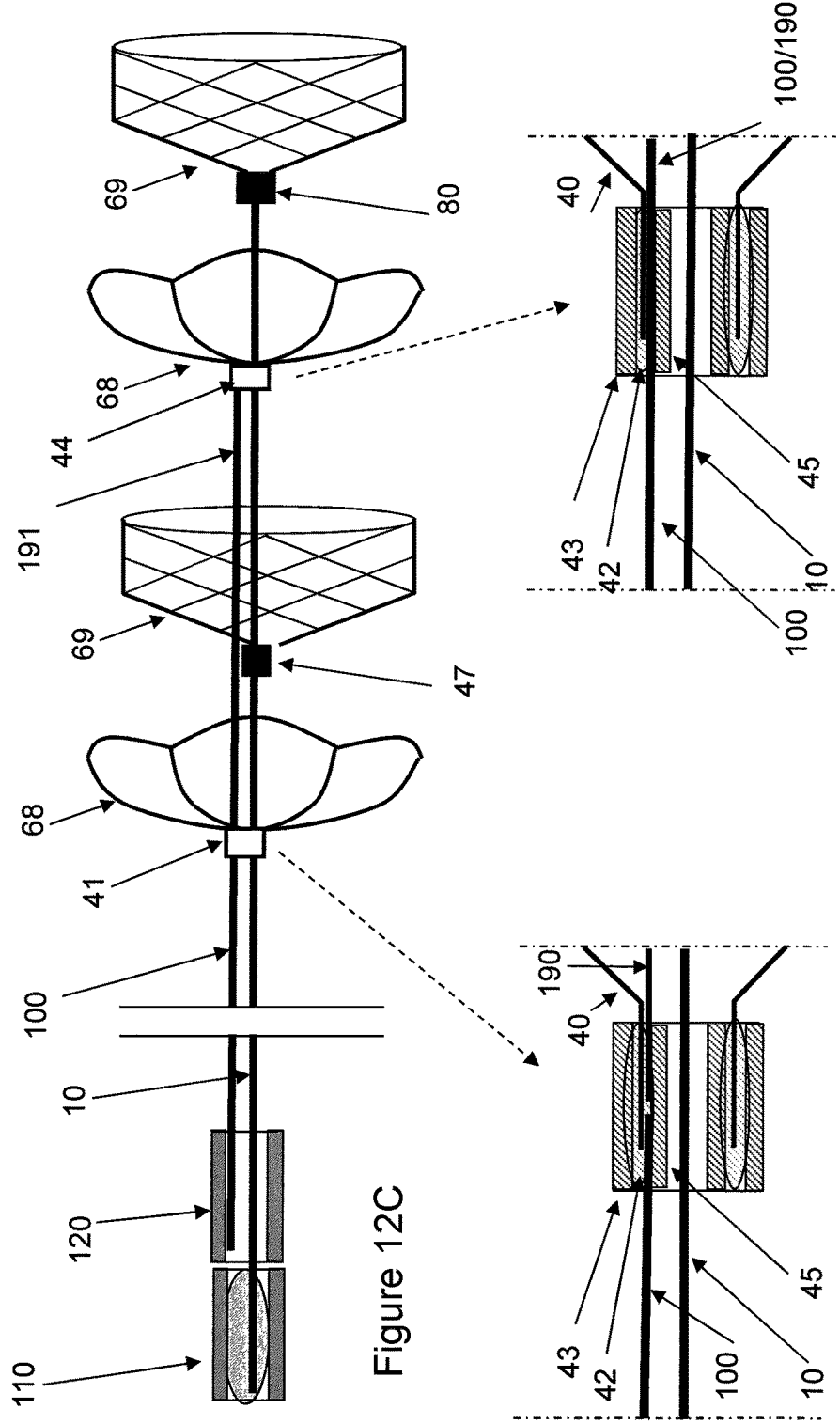

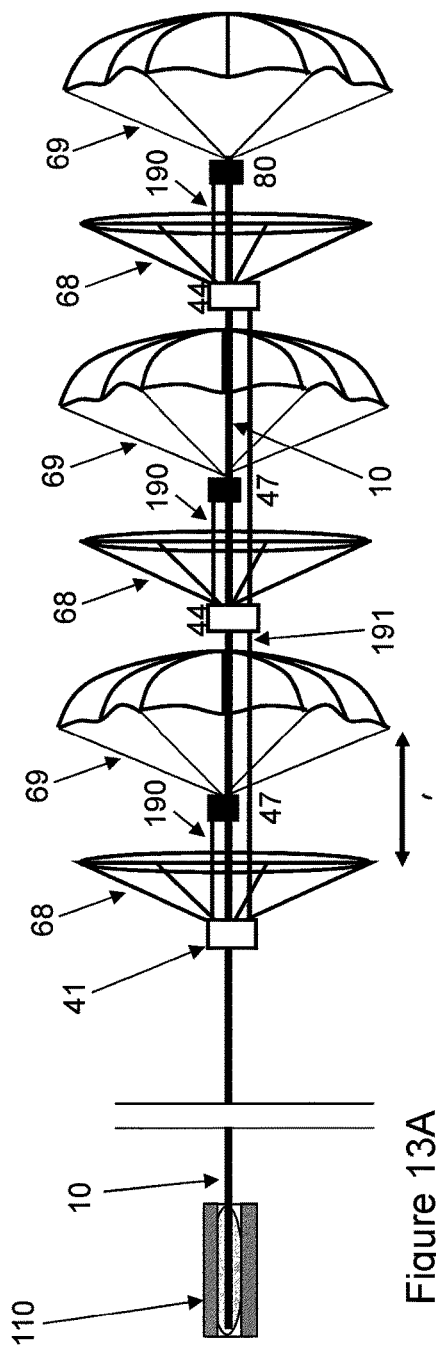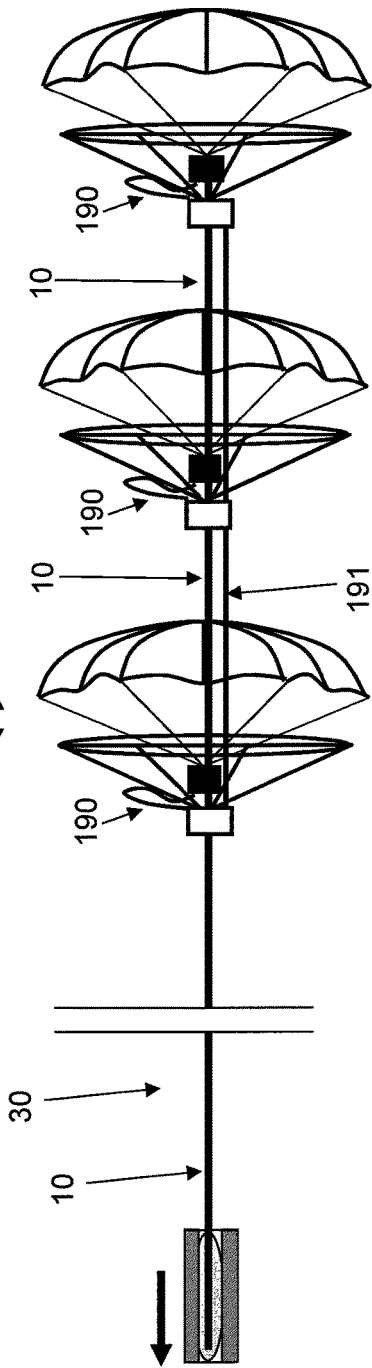
Figure 13A
Figure 13B

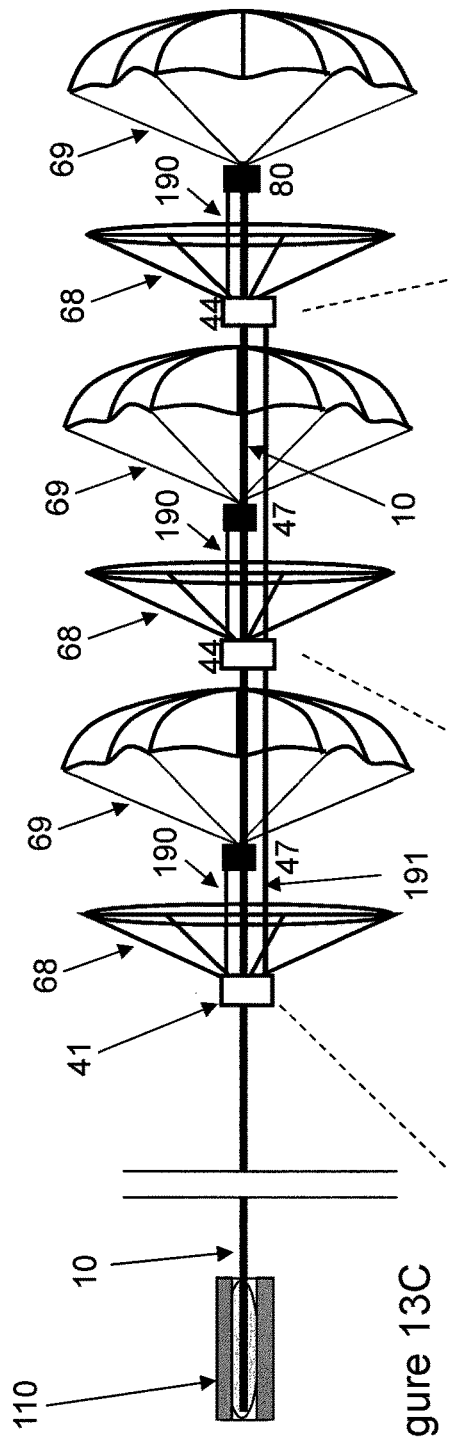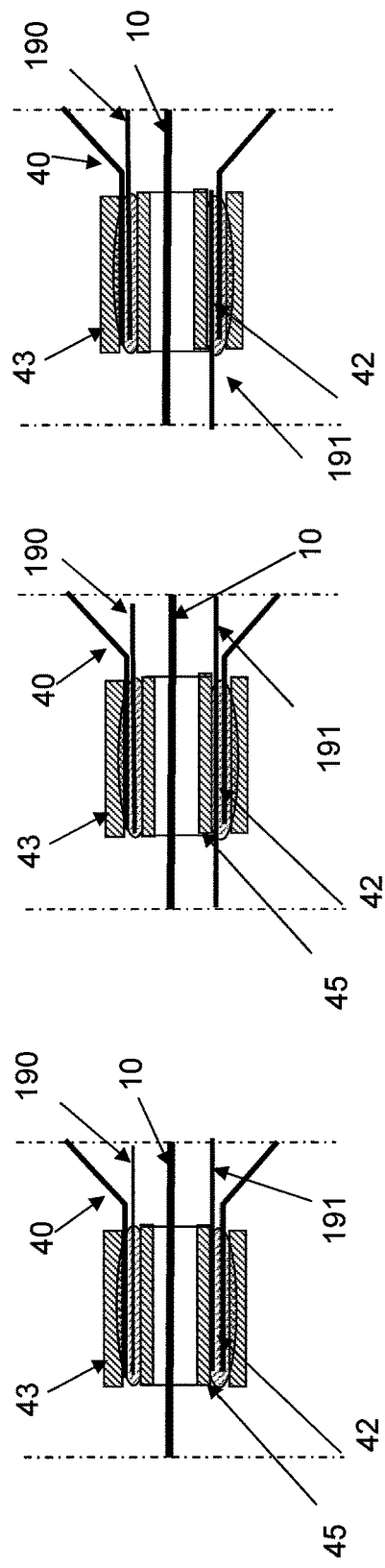
Figure 13C
Figure 13D
Figure 13E
Figure 13F

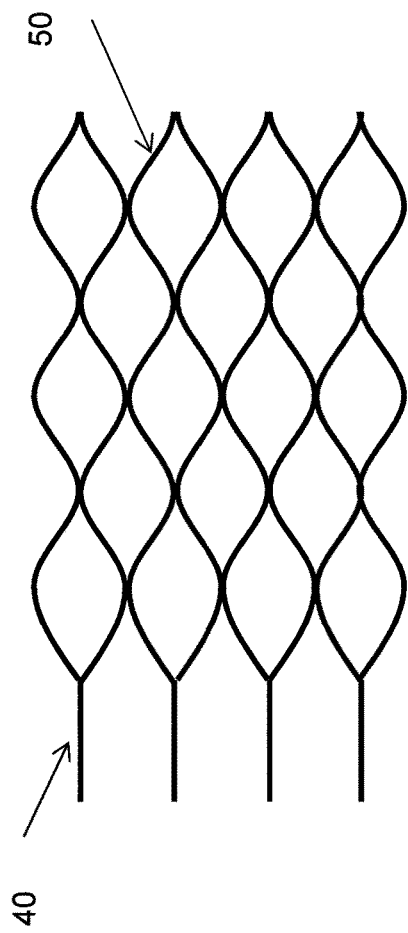
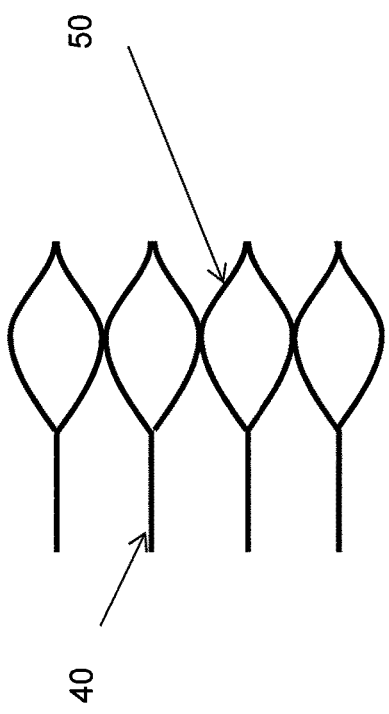
Figure 15A
Figure 15B

INTRAVASCULAR THROMBOEMBOLECTOMY DEVICE COMPRISING A PLURALITY OF CLOT ENGAGING ELEMENTS AND METHOD USING THE SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present disclosures are generally related to a device used in a body lumen such as a blood vessel and a method of using the same.

Description of the Related Art

A variety of disease conditions can be caused, at least in part, by blockage or, occlusions or clots of blood vessels. A well-known example of such conditions includes, but is not limited to stroke. Other such conditions include a myocardial infarction, limb ischemia, occlusions or clots of vascular grafts and bypasses, and venous thromboses.

A stroke is often referred as a "brain attack." It often results in rapid and significant loss of brain function due to disturbance in the blood supply to the brain. As a result, inabilities in movement, use of language, vision and many other biological functions may be temporarily or irreversibly impaired. Strokes are either hemorrhagic (due to bleeding) or ischemic (due to inadequate blood supply). The majority of strokes are ischemic. It is estimated that about 700,000 ischemic strokes occur in the United States annually. The major causes of an ischemic stroke include thrombosis (clotting) in a blood vessel supplying the brain or an embolus from another source such as the heart going to a blood vessel supplying the brain. Sometimes a thrombosis occurs where there is a pre-existing stenosis of blood vessels in the brain, usually from atherosclerotic disease.

Treatments for acute ischemic stroke are concentrated on re-establishing blood flow to the brain as quickly as possible. They include the use of a drug such as tissue plasminogen activator (tPA), a thrombolytic agent (clot-busting drug). More recently devices such as the Stentriever devices (Trevo, Stryker, Fremont, Calif.; Solitaire, Covidien, Irvine, Calif.) and suction thrombectomy catheters (Penumbra, Inc., Alameda, Calif.) have been approved by the Food and Drug Administration for thrombectomy in acute stroke. These devices do not always achieve complete recanalization. Sometimes they fail to open the vessel at all or may only partially open the vessel. They also may take some time to work, with multiple passes of the devices into the intracranial circulation needed before the vessel is reopened. In addition, they may fragment the clot and allow some portion of the clot to go out more distally in the cerebral circulation. There is a need for devices with high rates of complete recanalization, with complete or partial clot capture, performed in a more rapid manner.

SUMMARY OF THE INVENTION

One aspect of the invention disclosed herein relates to a device for use in a body lumen. The device may comprise a central wire comprising a proximal end and a distal end thereof and a plurality of engaging elements comprising a distal engaging element, a proximal engaging element, and one or more middle engaging element, each of the plurality of the engaging elements being associated with the central wire. Each of the plurality of engaging elements may comprise a distal end and a proximal end thereof. The distal engaging element is most distally located among the plurality of the engaging elements and fixed to a distal tip of the central wire, the proximal engaging element is most proximally located among the plurality of the engaging elements, and the one or more middle engaging element is located between the distal and proximal engaging elements. The device may further comprise a flexible connection wire that associates with the proximal engaging element and at least one more engaging element, said connection wire configured to space the associated engaging elements apart at a distance and a proximal end control element that is located proximal to the proximal engaging element, wherein the proximal end of the proximal engaging element is fixed at the proximal end control element.

In some embodiments, the proximal end control element may comprise a tubing compartment comprising a distal end and a proximal end thereof, and the proximal end of the proximal engaging element is fixed at about the distal end of the tubing compartment.

In some other embodiments, the proximal end control element may comprise a control wire comprising a distal end and a proximal end thereof, and the proximal end of the proximal engaging element is fixed at about the distal end of the control wire.

In still some other embodiments, the proximal end control element may comprise a wire comprising a distal end and a proximal end thereof, a distal segment of the wire is flexible serving as a connection wire, and all of the engaging elements are fixed to the connection wire.

In still some other embodiments, at least one of the plurality of engaging elements may comprise a plurality of wires or struts.

In still some other embodiments, an overall shape of the engaging elements is conical, spherical, tubular, ellipsoid or any combination of the above structures.

In still some other embodiments, the flexible connection wire associates with each of the plurality of the engaging elements at a pre-set distance.

In still some other embodiments, the flexible connection wire associates with each of the plurality of the engaging elements at an equal distance.

In still some other embodiments, at least one of the plurality of engaging elements is self-expandable.

In still some other embodiments, at least one of the plurality of engaging elements comprises about 3 mm to about 25 mm in length between the respective proximal and distal ends.

In still some other embodiments, at least one of the plurality of engaging elements has an open end at its distal end.

In still some other embodiments, a degree of stiffness of each of the plurality of engaging elements is identical to or different from each other.

In still some other embodiments, a dimension such as diameter and length of each of the plurality of engaging elements is identical to or different from each other.

In still some other embodiments, at least one of the plurality of engaging elements has a closed end at its distal end.

Another aspect of the invention disclosed herein may relate to a device for use in a body lumen. The device may comprise a central wire comprising a proximal end and a distal end thereof and a plurality of engaging elements comprising at least two pairs engaging elements, each of the plurality of the engaging elements associated with the central wire. Each pair of the engaging elements may comprise a capture element and a receiving element, the capture element located distal to the receiving element in each pair. The device may further comprise a spacing wire that associates with the proximal element and the receiving element spacing the associated proximal element and the receiving element in each pair at a distance and a proximal end control element that is located proximal to all of the engaging elements, wherein the proximal end of the most proximal engaging element is fixed at the proximal end control element.

In some embodiments, the engaging elements in each pair may operate together as a retrieval unit.

In some other embodiments, the proximal end control element may comprise a tubing compartment comprising a distal end and a proximal end thereof, and the proximal end of the most proximal engaging element and the spacing wire may be fixed at about the distal end of the tubing compartment.

In still some other embodiments, the proximal end control element may comprise a control wire comprising a distal end and a proximal end thereof, and the proximal end of the most proximal engaging element may be fixed at about the distal end of the control wire.

In still some other embodiments, the proximal end control element may be a wire comprising a distal end and a proximal end thereof, a distal segment of the wire may be flexible serving as a spacing wire, and all of the receiving engaging elements may be fixed to the spacing wire.

In still some other embodiments, at least one of the plurality of engaging elements may comprise a plurality of wires or struts.

In still some other embodiments, an overall shape of the engaging elements may be conical, spherical, tubular, ellipsoid or any combination of the above structures.

In still some other embodiments, at least one of the plurality of engaging elements may be self-expandable.

In still some other embodiments, at least one of the plurality of engaging elements may comprise about 3 mm to about 25 mm in length between the respective proximal and distal ends.

In still some other embodiments, at least one of the plurality of engaging elements may have an open end at its distal end.

In still some other embodiments, a degree of stiffness of each of the plurality of engaging elements may be identical to or different from each other.

In still some other embodiments, a dimension such as diameter and length of each of the plurality of engaging elements may be identical to or different from each other.

In still some other embodiments, at least one of the plurality of engaging elements may have a closed end at its distal end.

In still another aspect of the invention disclosed herein relates to a device for use in a body lumen. The device may comprise a central wire comprising a proximal end and a distal end thereof and a plurality of engaging elements comprising at least two pairs of the engaging elements, each of the plurality of the engaging elements being associated with the central wire. Each pair of the engaging elements may comprise a capture element and a receiving element, the capture element located distal to the receiving element in each pair. The device may further comprise a spacing wire that associates with the proximal element and the receiving element spacing the associated proximal element and the receiving element in each pair at a distance. One or more of the receiving element may be fixed to the spacing wire with a tubing connector that can freely slide on the central wire.

In some embodiments, the device may further comprise a connection wire that is fixed between the capture element and receiving element of each pair of engaging elements.

In some other embodiments, at least one of the plurality of engaging elements may comprise a plurality of wires or struts.

In still some other embodiments, an overall shape of the engaging elements may be conical, spherical, tubular, ellipsoid or any combination of the above structures.

In still some other embodiments, at least one of the plurality of engaging elements may be self-expandable.

In still some other embodiments, at least one of the plurality of engaging elements may comprise about 3 mm to about 25 mm in length between the respective proximal and distal ends.

In still some other embodiments, at least one of the plurality of engaging elements may have an open end at its distal end.

In still some other embodiments, a degree of stiffness of each of the plurality of engaging elements may be identical to or different from each other.

In still some other embodiments, a dimension of each of the plurality of engaging elements may be identical to or different from each other.

In still some other embodiments, at least one of the plurality of engaging elements may have a closed end at its distal end.

In still some other aspect of the invention disclosed herein relates to a method of removing at least part of an occlusion from a first location in a body lumen. The method may comprise introducing a device according to some embodiments disclosed herein into the body lumen, locating the device at about the first location, engaging at least part of the occlusion with at least one of the plurality of the engaging elements, and removing the engaged occlusion from the first location.

In some embodiments, the engaging may comprise adjusting the position of one or more of the plurality of the engaging elements by holding the proximal end control element while pulling the central wire to engage the occlusion between at least two engaging elements, and/or holding the central wire while pushing the proximal end control element to engage the occlusion between at least two of the engaging elements.

In some other embodiments, the engaging may comprise adjusting the position of the receiving elements and or the capture elements by holding the proximal end control element while pulling the central wire to engage the occlusion between at least one pair of the engaging unit, and/or holding the central wire while pushing the proximal end control element to engage the occlusion between at least one pair of the engaging unit.

In still some other embodiments, the engaging may comprise adjusting a position of the capture element by pulling the central wire until at least a part of clot is engaged between at least one pair of the engaging unit.

BRIEF DESCRIPTION OF THE DRAWINGS

FIGS. 2A-C show another non-limiting, illustrative example of a device according to some embodiments of the invention, particularly when the device is located in a body lumen, and illustrates some non-limiting examples of a mechanism to remove an occlusion/clot from a blood vessel according to some embodiments of the invention.

FIGS. 5B-D also show the relationship among the connectors, control tubing apartment, central wire, and connection wire.

FIGS. 7A-C show still other non-limiting embodiments of a device according to the invention where the device comprises a plurality of engaging elements. The device may further comprise a control wire, an alternative to the tubing compartment. In the embodiments shown in FIG. 7A, the device comprises a connection wire and a control wire. The connection wire and the control wire may be joined at the proximal end of the proximal engaging element. The control wire may be operably connected to a control wire handle at the proximal end of the device. FIG. 7B shows certain, non-limiting embodiments of a proximal connector that may join the control wire, the connection wire and the legs of the proximal engaging element inside the proximal connector. Alternately, a separate connection wire may not be necessary in some of such embodiments. Therefore, as illustrated in FIG. 7C, the control wire and the connection wire can be from the same piece of wire, with the connection wire section/segment being small and flexible and the control wire segment being slightly larger and pushable. The control/connection wire and the legs of the proximal engaging element may be joined via a connector FIG. 8A shows still another non-limiting embodiment of a device according to the invention where the device comprises a plurality of engaging elements. Among the plurality of engaging elements, some of them are configured to function as a receiving element whereas some other are configured to function as a capturing/cinching element. Each receiving element and a capture element form an engaging unit/pair. In certain embodiments, the receiving elements may be associated with or connected to a spacing wire. The spacing wire and the proximal end of the proximal element are connected to a control tubing compartment. In some embodiments, a pair of a receiving element and a capturing element may function as an engaging unit/pair. In certain embodiments, the device may comprise a plurality of engaging units/pairs. FIG. 8A shows the engaging units/pairs are open, and FIG. 8B shows the engagement units/pairs are closed, i.e. the spacing between the capture engaging element and receiving engaging elements are shortened. FIGS. 8 C-F show the detailed connector structures and their relationship with the control tubing apartment, central wire, and spacing wire.

FIGS. 9A-C shows an embodiment where a relatively large occlusion is removed by the device comprising a plurality of operation units/pairs. FIGS. 9D-F shows an embodiment where more than one occlusion are removed individually by multiple operation units/pairs.

FIGS. 12A-E show still another non-limiting embodiment of a device according to the invention where the device comprises a plurality of engaging elements, some of which may function as a receiving elements whereas some other of which may function as a capturing/cinching element. In addition, the device may further comprise a control wire. The control wire, in some embodiments, may be operably connected to a handle at the proximal end of the device with which an operator can manipulate the control wire, e.g. pushing or pulling the control wire. All the receiving elements are fixed to the spacing wire with designed spacing in between and they can move freely along the central wire. All the capturing elements are fixed to the central wire. By controlling one or both of the control wire and the central wire, the space between the engaging elements can be adjusted so as to maximize the engagement and containment of an occlusion by the device. FIGS. 12A and 12B show the adjustment of the space between the engaging elements. FIGS. 12D-E show views of certain, non-limiting embodiments of a proximal connector.

FIGS. 13A-F show still alternative non-limiting embodiments of a device according to the invention where the device comprises a plurality of engaging elements. In certain embodiments, two engaging elements, one being a receiving element and the other being a capturing element, form an individual operation unit/pair. The device can comprise multiple engaging operation units/pairs. The receiving elements in different operation units/pairs can be associated with or connected to a connection wire. In addition, in certain embodiments, the engaging elements in a same unit/pair (e.g. at least one receiving element and one capturing element) may be connected to or associated with a spacing wire. FIG. 13B shows the device where the spaces between the engaging elements are reduced. FIGS. 13 D-F show the relationship of the connectors with the engagements elements, connection wires, spacing wires and central wire at various locations of the engagement compartment.

FIGS. 15 A-B show still another alternative, non-limiting illustrative embodiments of structures that an engaging element can be made from.

REFERENCE NUMERALS FOR DESIGNATING MAIN COMPONENTS IN THE DRAWINGS

Figure 1A:
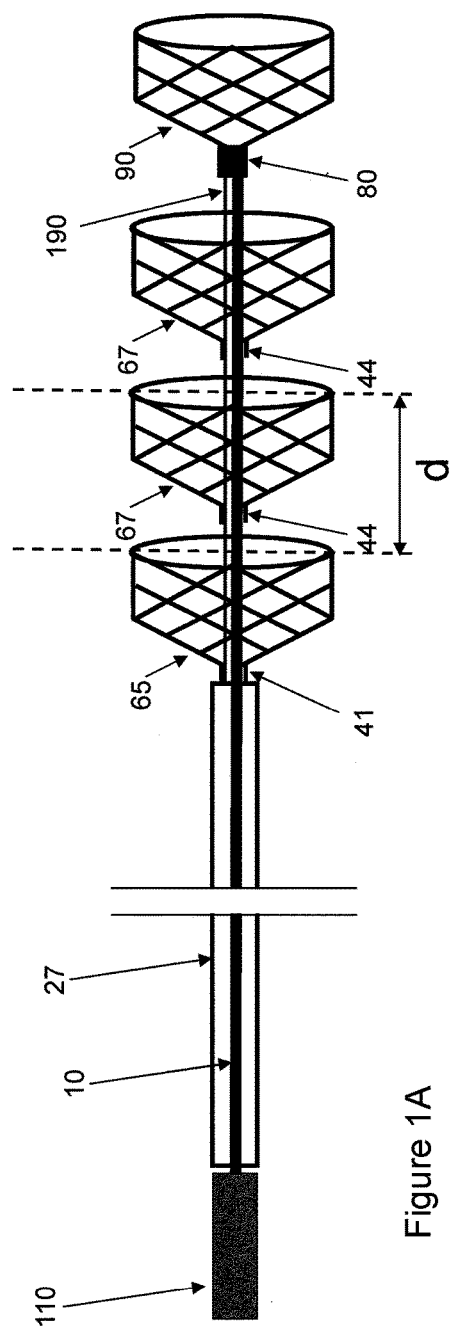
FIGS. 1A-B show a non-limiting, illustrative example of a device according to some embodiments of the invention.

1: Body lumen surface
10: Central wire
21: Inner pusher tubing
23: Outer pusher tubing
25: Proximal pusher tubing
27: Pusher tubing/control tubing apartment
30: Microcatheter
40: Engaging element leg
41: Proximal element connector (freely slide on central wire)
42: joining media
43: outer element connector tubing
44: middle/Intermediate element connector (freely slide on central wire)
45: Inner element connector tubing
47: Capturing engaging element connector (fix engaging element onto central wire)
50: Engaging element body
60: Occlusion/Clot
65: Proximal engaging element
67: middle/Intermediate engaging element
68: Receiving element
69: Capturing element
80: Distal element connector
90: Distal engaging element
100: Control wire
110: central wire handle
120: Control wire handle
150: Distal element tip connector
190: Connection wire
191: Spacing wire

DETAILED DESCRIPTION OF THE EMBODIMENTS

The present disclosure is generally related to a device used in a body lumen, such as a blood vessel, and a method of using the same. In some embodiments, the device may be positioned in the body lumen to remove occluding substances such as a blood clot, or foreign body from the lumen. Some aspects of the present invention provide a device and method that are configured to treat conditions in blood vessels which include, but are not limited to, a stroke. In some embodiments, the device and method are configured to treat conditions related to an ischemic stroke by removing an occlusion/clot from a blood vessel and/or reopen a blood vessel and resume blood flow therein. Non-limiting examples of blood vessels may include: an artery, a vein or a surgically implanted graft and bypass serving as a component of the circulatory system.

The term "occlusion" or "clot" generally includes any matter partially or completely obstructing a lumen of the blood vessel. The occlusion/clot slows or obstructs a flow (e.g. a stream of blood or any other biological fluid) running through the lumen. Examples of the occlusion/clot may include blood occlusions/clots and atherosclerotic plaques present in the vessel as well as fat or foreign bodies.

The term "stroke" generally includes a condition(s) that is in part caused due to disturbance in blood supply to a brain. The disturbance can be caused by blockage (e.g. ischemic stroke) and/or hemorrhage (e.g. hemorrhagic stroke). In particular, an ischemic stroke can be caused due to partial or substantial occlusion of a blood vessel. Treatment of the ischemic conditions can be applied to blood vessels present in the brain as well as in other tissues such as the heart. Accordingly, the device and method disclosed in this application are not limited to use in any particular organs but can be applied to any blood vessel of the body that would benefit from removal of an occlusion/clot to restore blood flow. In addition, the device and method according to the present invention can be used to treat venous occlusions/clot which may result in other conditions besides ischemia.

The device can be introduced into the blood vessel through a catheter or microcatheter. The "catheter" or "microcatheter" generally includes a tubular structure that can be inserted into a body lumen, thereby allowing administration of a device and/or chemicals to a body area that needs treatment.

Furthermore, many different modifications and alternations, which should be obvious to a person with ordinary skill in the art, can also be done without affecting the scope of the invention to properly serve the specific treatment conditions. Therefore, not only the examples disclosed in this application but also such an obvious modification and alteration should also be included in the scope of the invention.

One aspect of the present invention is related to a device for use in a blood vessel comprising multiple engaging elements, a control tubing compartment, a central wire, and or a control wire. The engaging elements form a self-expanding compartment.

The sizes of blood vessels vary enormously, from a diameter of about 0.03 inch (about 1 mm) in smaller arteries and veins to 1.2 inches (about 30 mm) in the aorta. Accordingly, in some embodiments, the diameter of the device may range from approximately 0.01 inch (about 0.25 mm) to 1.2 inches (about 30 mm) when it is an in an expanded state. In some other embodiments, the diameter of the device in a collapsed state may range from approximately 0.01 inch, approximately 0.02 inch, approximately 0.03 inch, approximately 0.04 inch, approximately 0.05 inch, approximately 0.06 inch, approximately 0.07 inch, approximately 0.07 inch, approximately 0.08 inch, approximately 0.09 inch, approximately 0.10 inch, approximately 0.12 inch, approximately 0.14 inch, approximately 0.16 inch, approximately 0.18 inch, approximately 0.20 inch, approximately 0.30 inch, approximately 0.40 inch, approximately 0.50 inch, approximately 0.60 inch, approximately 0.70 inch, or any range between the above-listed values.

Another aspect of the present invention is related to a device for use in a blood vessel comprising a microcatheter, a central wire, a tubing component, and an engaging compartment. The engaging compartment may comprise a distal engaging element, middle engaging element(s), and a proximal engaging element. The engaging element can be linked with connection wire and/or spacing wire via connectors. In some embodiments, the distal engaging element may be associated with the central wire. The space(s) between the engaging elements may be adjustable. The space between adjacent elements can be adjusted approximately from 0 to 50 mm in at least some embodiments. In certain embodiments, the distance between the engaging elements may be adjusted approximately 0 mm, 5 mm, 10 mm, 15 mm, 20 mm, 25 mm, 30 mm, 35 mm, 40 mm, 45 mm, and 50 mm, and any range there between. In alternative embodiments, the space between the engaging elements may be adjusted to be more than 50 mm.

In some embodiments, the device can be introduced into a blood vessel. The sizes of blood vessels vary enormously, from a diameter of about 0.03 inch (about 1 mm) in smaller arteries and veins to 1.0 inch (about 25 mm) in larger arteries. Accordingly, in some embodiments, the diameter of the device may range from approximately 0.01 inch (about 0.25 mm) to 1.0 inch (about 25 mm). Also, the diameter of a single device may vary during the operation as the engaging compartment gets opened (or expanded) or closed (or collapsed).

In some embodiments, the device further comprises a central wire. The central wire may pass through the tubing component and move freely there through. In certain embodiments, the central wire is associated with the engaging compartment. More particularly, the central wire may be associated with the distal engaging element, middle element(s) and the proximal engaging element. Association generally refers to any type of connection between two objects. Association includes fixation in that when two objects are associated, movement of one object would be hindered by another object. In other words, once the two objects are associated in a way of fixation, movement of two objects would be synchronized. However, association does not necessarily indicate fixation of one object to another. Accordingly, when two objects are associated but not in a state of fixation, movement of one object with respect to the other object would not be hindered. Therefore, the middle element(s) and the proximal engaging element may be associated with the central wire (for example, they may pass along the central wire), but they may move freely along the central wire, in at least some embodiments.

According to certain embodiments, the central wire is fixed or joined with the distal engaging element. In some occasions, the proximal end or the distal end of the distal engaging element may be joined to the distal end of the central wire. The association (i.e. connection) between the central wire and the distal engaging element may be done via various ways such as welding, gluing, or clipping on to connectors. In some embodiments, the joint between the central wire and the distal engaging element is covered by a distal element connector. Alternatively, a connecter may consist of a short outer connector tube and a short inner connector tube with the component to be fixed between the walls of tubing and filled with joint media.

In some embodiments, the central wire may comprise or in be in the form of a wire, braid, or cable. The wire may have a uniform diameter or tapered diameter, which varies from distal to proximal ends. Various materials can be used to manufacture the central wire, which may include metal and non-metal materials. Some non-limiting examples of metal materials for the central wire may comprise nickel, titanium, stainless steel, cobalt, chrome and any alloys of the foregoing such as Nitinol (NiTi), or Cobalt Chromium alloys. In addition, any polymers or plastics which have desired properties of being the central wire can be used for production of the same. Polymers include, but are not limited to, Polyimide, PEEK (Polyether ether ketone), Nylon, PTFE (polytetrafluoroethylene), PET (Polyethylene terephthalate), Polypropylene, etc. Polymer coated metal including but not limited to, PTFE coated Stainless Steel, or PTFE coated NiTi can also be used as a central wire. Also a hydrophilic coating would be applicable. Such coating can be applicable in part to reduce friction between the central wire and the tubing compartment(s). The central wire can also be made of composite materials, such as PTFE or FEP (Fluorinated ethylene propylene) tubing over NiTi wire, or PTFE or FEP tubing over Stainless Steel etc. The diameter of the central wire may range approximately from 0.001 inch to 0.1 inch. In certain embodiments, the diameter of the central wire may be about 0.001, 0.002, 0.003, 0.004, 0.005, 0.006, 0.007, 0.008, 0.009, 0.01 inch. Alternatively, the diameter of the central wire may be more than 0.01 inch.

The term "engaging compartment" generally includes elastic structure(s) that can be compressed into small profile/diameter and inserted into a body lumen through microcatheter, and, upon releasing compression, expands to a larger diameter to engage and remove at least part of clot/occlusion in order to recanalize the blocked lumen or vessel. The engaging compartment may comprise a distal engaging element, middle engaging element(s), and a proximal engaging element. In some embodiments, the engaging element may comprise a plurality of wires. Engaging elements can be formed into a mesh or a braid structure in at least some embodiments. In some other embodiments, the engaging element may comprise struts made from tubing or sheet materials. They can be made through laser cut hypo-tubes or sheet material, or photo etched sheet materials. Heat treatment may be needed to set them into the desired shape, e.g. cone shape or cylinder shapes, followed by chemical etching or electro-polishing in order to smooth the surface of the element.

The engaging elements can be made of elastic materials. Some non-limiting examples of such metal materials for engaging elements include nickel-titanium (NiTi) alloy, stainless steel, titanium and its alloys, and cobalt chrome (CoCr) alloys. Alternatively, any polymers or plastics which have desired properties for a distal engaging element can be used. In further alternative examples, the engaging elements can be constructed using two or more different materials, such as polymer coated metal materials.

In some embodiments, an overall all diameter of the engaging elements may vary from approximately 1 to 8 mm at its expanded state. In certain embodiments, the diameter of the distal engaging elements at their expanded state may be approximately 1 mm, 2 mm, 3 mm, 4 mm, 5 mm, 6 mm, 7 mm, and 8 mm or any range there between. In some other embodiments, a length of each engaging element may vary from approximately 2 to 40 mm. In certain some embodiments, the length of each engaging element may be approximately 2 mm, 3 mm, 4 mm, 5 mm, 6 mm, 8 mm, 10 mm, 15 mm, 20 mm, 25 mm, 30 mm, 35 mm, and 40 mm or any range there between. Further, in alternative embodiments, the length of each engaging element may be more than 40 mm.

In some embodiments, markers may be added to the device. Such markers may include radiopaque materials which help monitor the position and or movement of the device in the body. Some non-limiting examples of radiopaque markers may comprise gold, gold alloys, CoCr alloy, platinum, or platinum alloys. Marker(s) can also be in form of radiopaque coating. The markers may be added anywhere in the device. In some embodiments, one or more markers may be added at the distal engaging element so that a location of the distal engaging element in the body would be determined. In some other embodiments, one or more markers may be added at the proximal engaging element so that a location of the proximal engaging element in the body would be determined. In still some other embodiments, any or all engaging elements may contain markers. Alternatively, one or more markers may be added to the central wire and/or the tubing compartment. In some embodiments, the markers may be approximately 0.10 to 4 mm long, and the diameter is approximately 0.001 to 0.030 inch. However, any variations in any dimensions (e.g. length, diameter, size, and mass) and in shapes of markers are suitable.

In some embodiments, the device may comprise one or more tubing compartments. Control tubing compartments may comprise a plurality of tubing elements. Such tubing elements may include a pusher tubing and a connecting tubing. The pusher tubing may further comprise an inner pusher tubing, an outer pusher tubing, and/or a proximal pusher tubing, and distal pusher tubing in at least some embodiments. These pusher tubing components may be attached or fixed to each other. Various materials can be used to manufacture the tubing elements, which may include metal and non-metal materials. In some embodiments, the distal pusher tubing and/or an outer pusher tubing can be made from lubricious and flexible polymers such as PTFE or PET. Relatively small Polyimide or PEEK tubing may be utilized when stretch resistance is required. The proximal pusher tubing can be made from Nitinol super-elastic material, stainless steels, CoCr alloys, titanium alloys, or polymers (such as Polyimide, PEEK, etc.). To reduce friction between the pusher tubing and the inner lumen of microcatheter, one or more of the tubing elements can also be coated with lubricious material, such as PTFE coating, hydrophilic coating etc. The tubing elements can also be made of composite materials, such as PTFE or FEP (Fluorinated ethylene propylene) tubing over metal (Nitinol, stainless etc.) coil for pushability and flexibility.

The central wire, control wire, spacing wire, and connection wire can be in the form of a wire, braid, or cable. Some non-limiting examples of metal materials for the central wire may comprise nickel, titanium, stainless steel, cobalt, chrome and any alloys of the foregoing such as Nitinol (NiTi), Titanium alloys, or Cobalt Chromium alloys. In addition, any polymers or plastics which have desired properties of being the central wire can be used for production of the same. Polymers include, but not limited to, Polyimide, PEEK (Polyether ether ketone), Nylon, PTFE (polytetrafluoroethylene), PET (Polyethylene terephthalate), Polypropylene, etc. Polymer coated metal including but not limited to, PTFE coated Stainless Steel, or PTFE coated NiTi can also be used as a central wire. Also a hydrophilic coating can be applied to reduce friction between the wire and the inner lumen of pusher tubing.

In some embodiments, the outer diameter of the pusher tubing components may be approximately 0.001 to 0.050 inch. In other embodiments, the diameter of the pusher tubing components may be smaller than 0.001 inch or over 0.050 inch.

In some embodiments, the device may comprise a plurality of engaging elements such as two, three, four, five, six or more engaging elements. Therefore, in embodiments where three or more engaging elements are present in a device, there can be a distal engaging element that is located most distally among all engaging elements, a proximal engaging element that is located most proximally, and one or more middle engaging elements that are located between the distal and proximal engaging elements.

Figure 14E:
FIGS. 14A-E show still alternative, non-limiting and illustrative embodiments alternative structures of engaging elements.
Figure 14D:
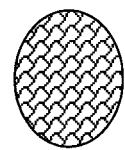
Figure 14C:
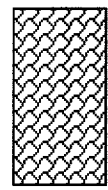
Figure 14B:
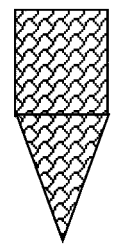
Figure 14A:
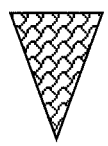

The shape, size, and structure/configuration of the engaging element are not limited and can be varied to a degree compatible with a blood vessel and suitable for treatment. In certain embodiments, the engaging element can be shaped generally in a conical or pyramid form (as shown in FIG. 14A), a cylindrical or tubular form (FIG. 14C), an ellipsoid (FIG. 14 D), or spherical form (FIG. 14D), or an umbrella (or parachute) form (FIG. 14E) etc., and combination of any of the form/shape described above. One example is shown in FIG. 14B. The engaging elements may be open or closed at either end when in a cylindrical or tubular form. Individual engaging elements present in a same device can vary from each other, e.g. in size, structure, material, and/or function. Alternatively, some or all of the engaging elements present in a same device can share one or more common features among, e.g. size, structure, material, and function.

In addition, in some embodiments, there is a connection wire that associates with two or more of the engaging elements of a device. In some embodiments, the connection wire may connect or associate with certain or some (not all) of a plurality of the engaging elements. In some other embodiments, the connection wire may associate or connect with all of the engaging elements present in the device. The association or connection between the connection wire and individual engaging elements may be fixed at a position of the connection wire. When multiple engaging elements are associated with (or connected to) a connection wire, the types of association/connection of an individual engaging element with the connection wire may vary within a single device, e.g. fixation or non-fixation manner. Thus, in some embodiments, some (not all) of the engaging elements that are associated or connected with a same connection wire may be fixed at their respective positions of the connection wire. The connection wire can be flexible, or floppy, which allows the space between engaging elements to be shortened when it is desired to bring the engaging elements closer together. In these circumstances the connection wire may be stretch resistant under tension so that the maximum distance between the engaging elements is also limited by the connection wire.

The association (i.e. connection) between the connection wire and the engaging element, especially the fixation (or joint) there between, may be done via various ways such as welding, gluing, or clipping. There can be an additional element such as a tubing or connector where the engaging element and the connection wire are fixed thereto. The association (i.e. connection) between the connection wire and the engaging element, especially where the engaging element can move along the central wire, can be done via various ways including a connector (e.g. a connector). For example, the engaging element may contain or be attached to a short inner element connector tubing and an outer element connector tubing. The connection wire may be attached between the walls of two tubing and the central wire may pass through (inside) the inner element connector tubing. Therefore, the engaging elements can move (slide) along the central wire without being fixed at a certain position.

In some designs, a spacing wire may also be present. Engaging elements can be fixed to the spacing wire. The spacing wire is slightly stiffer than the connection wire and therefore does not buckle or become slack. Thus it maintains a fixed space or distance between the engaging elements.

A connection wire and/or a spacing wire can be in the form of a round or flat wire, cable, or have a braid structure. The connection wire, in some embodiments, is flexible yet stretch-resistant. Some non-limiting examples of metal materials for the connection wire may comprise nickel, titanium, stainless steel, cobalt, chrome and any alloys of the foregoing such as Nitinol (NiTi), Titanium alloys, or Cobalt Chromium alloys. In addition, any polymers or plastics which have desired properties of being the connection wire can be used for production of the same. Polymers include, but not limited to, Polyimide, PEEK (Polyether ether ketone), Nylon, PTFE (polytetrafluoroethylene), PET (Polyethylene terephthalate), Polypropylene, etc. Polymer coated metal including but not limited to, PTFE coated Stainless Steel, or PTFE coated NiTi can also be used as a connection wire. Also a hydrophilic coating can be applied.

In certain embodiments, there can be more than one connection wire. In some of such embodiments, a connection wire may associate or connect with all of the engaging elements present in a device. Alternatively, a connection wire may associate or connect with a pair of engaging elements, i.e. a receiving engaging element and a capturing engaging element. In certain embodiments, there can be two, three, four, five, six or more connection wires present in a single device. In some other embodiments, a device can have seven or more connection wires.

In some embodiments, a device may comprise a proximal end control element that can associate with the most proximally located engaging element and be able to control the position of the associated engaging element(s). In certain embodiments, the proximal end control element can be a form of tubing compartment or a wire. The proximal end control element can set a boundary of the most proximal end of the engaging elements. In certain embodiments, the proximal end control element may be operably linked to a handle that can control the movement of the proximal end control element.

In some embodiments where a device comprises a plurality of engaging elements, the device may further comprise a tubing compartment that associates with (or connects to) a proximal engaging element of the device. In some embodiments, other engaging elements, besides the proximal engaging element, can be associated with (or connected to) the tubing through either a connection wire or spacing wire (both of which may help maintain a desired space between the proximal engaging elements and other engaging elements). In some embodiments, the proximal engaging element can be fixed at about the distal end of the tubing compartment via its proximal end connector. Therefore, in such embodiments, the movements of the proximal engaging element and other elements fixed to the connection wire or spacing wire are controlled by the tubing compartment.

In alternative embodiments, a device may comprise a plurality of engaging elements and also a control wire that associates with (or connects to) one or more engaging elements of the device. In some embodiments, the control wire may associate with a proximal engaging element of the device. The association (or connection) between the control wire and the proximal engaging element(s) may comprise a fixation or joint that the engaging element is fixed at a position of the control wire. Therefore, the movement of the proximal engaging element is controlled by pushing or pulling the control wire.

In certain embodiments where more than one engaging elements are associated with a control wire, each of the associated engaging elements can be fixed at its respective position on the control wire. In some embodiments where multiple engaging elements (receiving elements) are associated with the control wire, some (not all) of the associated engaging elements are fixed at their respective position on the control wire, or spacing wire via engaging element connector tubing. These engaging elements can move along the central wire to change the spaces between the receiving elements and the capture elements.

In some embodiments, a control wire is operably linked or connected to a handle at the proximal end of the device such that an operator (e.g. a medical practitioner) can control (or mobilize) the control wire via the handle, e.g. pushing or pulling the control wire. This control operation, which controls the movement of the control wire, will result in controlling the movement of engaging elements that are associated with the control wire and the spacing wire.

A control wire can be in the form of a wire, cable, braid, or tubing. Some non-limiting examples of metal materials for the connection wire may comprise nickel, titanium, stainless steel, cobalt, chrome and any alloys of the foregoing such as Nitinol (NiTi), Titanium alloys, or Cobalt Chromium alloys. In addition, any polymers or plastics which have desired properties of being the control wire can be used for production of the same. Polymers include, but not limited to, Polyimide, PEEK (Polyether ether ketone), Nylon, PTFE (polytetrafluoroethylene), PET (Polyethylene terephthalate), Polypropylene, etc. Polymer coated metal including but not limited to, PTFE coated Stainless Steel, or PTFE coated NiTi can also be used as a control wire. Also a hydrophilic coating can be applied.

In some embodiments, individual engaging elements can be associated with (or connected to) one or more of the wires selected from the group consisting of a control wire, a connection wire, a spacing wire, and a central wire. In addition, when an individual engaging element is associated with (or connected to) at least two of the wires, the engaging element can be fixed at a position with respect to at least one of the associated/connected wire(s) while movable along the other associated/connected wire(s). Thus, for example, if an engaging element is associated with a control wire or a spacing wire i.e. fixed to the control wire or a spacing wire, it can still be movable on the other wire.

When individual engaging element(s) are associated with (or connected to) one or more wires (e.g. a control wire, a connection wire, a spacing wire, and a central wire), by controlling one or more of such wires, the position of individual engaging element can be controlled. In addition, the space or distance between the engaging element(s) can also be adjusted via the control of their respectively associated/connected wire(s). Accordingly, while attempting to engage and contain an occlusion with the device so as to remove or treat the occlusion from a body lumen, an operator can mobilize a single engaging element or two or more engaging elements as an operation unit/pair. This complex and fine mode of operation significantly enhances the efficiency of the treatment while minimizing a risk of damaging the body lumen.

A control wire (or tubing compartment) may be separate from and not attached to a central wire and therefore move independently. In some embodiments, there are separate proximal handles that are configured to control the control wire or tubing compartment, and the central wire. These handles act as a controller. By operating these handles and controlling the central wire and the control wire or tubing compartment, individual engaging elements of a device can be positioned in a desired location, and also the space/ distance between two or more of the engaging elements can be adjusted so as to maximize the grabbing/capturing/removal of an occlusion from the body lumen. Alternatively, or in combination with a control wire or tubing compartment, and a central wire, the connection wire and, or spacing wire in certain embodiments is also able to control a space or distance between two or more engaging elements. For example, the connection wire may be separate from the central wire and control wire and move independently. Therefore it may allow the space/distance between one or more engaging elements to be shortened. When the central wire is pulled proximally or the control wire or tubing compartment is pushed distally, the space between the receiving elements and the capturing elements will be shortened so as to cinch or hold a clot. While pulling the control wire or tubing compartment proximally and holding the central wire, the distance between the capturing elements and the receiving elements increase until the connection wire is under tension. This allows the components of the engagement compartment to be withdrawn back into the microcatheter without elements being overlapped with each other.

In some embodiments, a device may comprise two or more engagement units/pairs in which four or more engaging elements operate together to capture/cinch an occlusion and remove it from a body lumen. In certain embodiments, the engaging unit/pair may comprise two engaging elements, one functions as a receiving element and the other functions as a capturing element. In some embodiments, a capturing element can be located distally whereas a receiving element can be located proximally in an engagement unit/pair. The capturing element may be formed in a manner that can engage (e.g. capture, or grab,) an occlusion. The capturing element can engage the occlusion directly with its proximal ends of the element body or by its wire/strut structure along any parts of the struts that come into contact with the occlusion. Alternatively, the occlusion can be frictionally engaged between a body lumen and the capturing element. Still alternatively, the occlusion can be captured, cinched or held between the capturing element and the receiving element. All of these mechanisms for capturing, engaging, cinching or holding of the occlusion may be working simultaneously to engage and remove the occlusion, e.g. part of the occlusion may be frictionally engaged with (between) the capturing element and the body lumen and some other part of the occlusion may be engaged with the receiving element. There can be various modes of capturing or engagement of an occlusion using the plurality of engaging elements and the body lumen and any of such variations are encompassed within the scope of the method and device disclosed herein.

In certain embodiments, the distal engaging element may comprise a plurality of wire or struts forming a web such that it can capture the occlusion on its own or in combination with another proximally located engaging element or receiving element and/or the body lumen. The more proximal engaging element or receiving element, although it can also be able to engage directly with the occlusion if desired or necessary via its wires or struts, can also function to ensure or strengthen the engagement of the occlusion by the more distal engaging or capturing element. For example, in certain cases where an occlusion is relative large or extends a distance along the body lumen, multiple engaging elements or multiple capturing and receiving elements (and often along with a frictional engagement with a body lumen) can act to engage the occlusion at more than one location to ensure more complete engagement of the clot. See, e.g. a non-limiting and illustrative embodiment shown in FIG. 2B and FIGS. 9A-C. Alternatively, an individual engagement (or operation) unit/pair separately operates to remove a separate occlusion. See, e.g. a non-limiting and illustrative embodiment shown in FIGS. 9 D-F. Also, alternatively or in combination with at least one of the foregoing modes, the receiving element or more proximal engaging element can move close to the capturing element or more distal engaging element holding or cinching the clot between the two adjacent elements, which may result in a more complete or stronger capture of the occlusion. In certain embodiments, the proximal engaging elements or receiving elements may be shaped in a manner that it can conform to a proximal portion of the more distal engaging element or capturing element. In other words, the proximal portion of the distal engaging element or capturing element may fit within the distal portion of the more proximal engaging element or receiving element. Therefore, the containment of the occlusion between the two elements can be further secured during the treatment procedure and also during the removal of the device from the lumen.

In some embodiments, a device can comprise more than two operation units/pairs. Therefore, in certain embodiments, the device may comprise three, four, five, six or more operation units/pairs. In certain embodiments, the distal engaging element or the distal end of the device may not fully pass beyond an occlusion in a body lumen. Rather, the device may proceed into only part of the proximal end of the occlusion, e.g. as seen in FIG. 9A-F, and engage only part of the occlusion. For example it may be difficult or impossible to visualize how long the blockage (occlusion) extends in the lumen i.e. where the distal end of the occlusion is. In these situations it may be judged to be safer to advance the device by or within only part of the occlusion and also engage only the part of the occlusion. However, in some other occasions the device may be advanced beyond the distal end of the occlusion when it is judged that this may be a safe maneuver.

In some embodiments, the position of an individual engaging element or the position of an operation unit/pair can be adjusted via movement of at least one selected from the group consisting of a central wire, a control tubing/wire compartment(s), a connection wire(s), a spacing wire(s), and a control wire(s). Generally, all the engaging elements in a device may be associated with (or connected to) a central wire. In some embodiments, only some (not all) of the engaging elements may be fixed at their respective position on the central wire whereas some other engaging elements may still be movable along the control wire. In certain embodiments, all the capturing elements of the device (from different operation units/pairs) may be fixed at their respective position in the central wire whereas all the receiving elements may be movable along the central wire For the purpose of illustration, some non-limiting and illustrative examples of the device according to the invention are provided in the following figures. While only few exemplary applications are described herein for the purpose of illustration, many different modifications and alternations, which should be obvious to a person with ordinary skill in the art, can also be done without affecting the scope of the invention. Therefore, not only the examples disclosed in this application but also such obvious modifications and alterations should also be included in the scope of the invention.

Figure 1B:
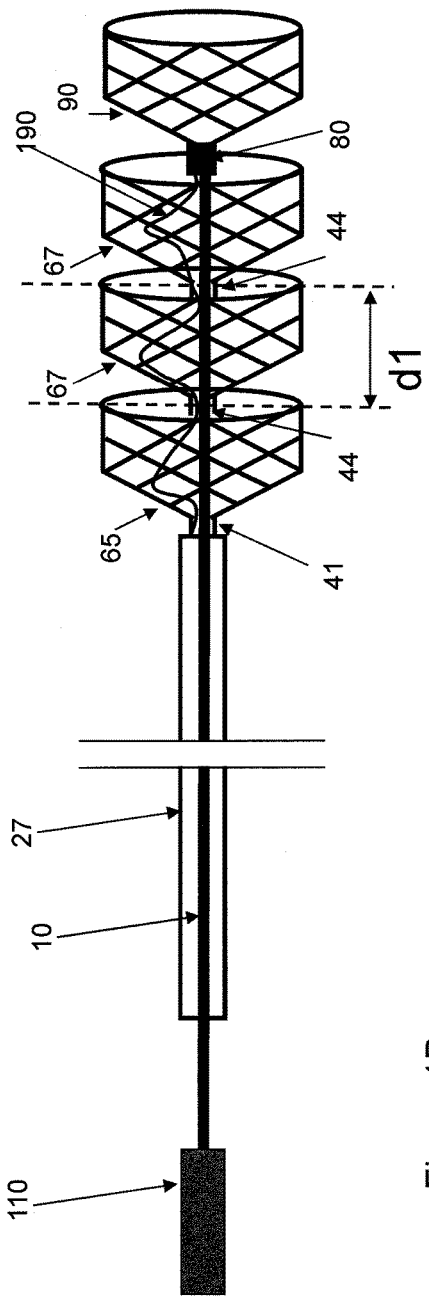

FIG. 1 illustrates one embodiment of a device where the device may comprise a plurality of engaging elements. In some embodiments, the device may comprise three or more engaging elements. In some embodiments, the device may comprise a central wire (10), a tubing compartment (27), three or more engaging elements (65, 67, 90), a connection wire (190). This figure shows four engaging elements, including a distal engaging element (90), a proximal engaging element (65), and two middle engaging elements (67). In this example the most distal engaging element (90) functions as a capturing element and all the engaging elements proximal to this may function as either capturing elements and/or receiving elements. The individual engaging element may vary from 3-25 mm in length when extended. FIG. 1A is the in its open state i.e. spaces between each adjacent engaging element are fully open, the length of the space is marked as "d". FIG. 1B is at its closed state, i.e. the spaces between each engaging elements are shortened (from "d" to "d1") for the purpose of holding, cinching or grabbing the occlusion or clot.

In some embodiments, all the multiple engaging elements (65, 67, and 90) are associated with (or connected to) the central wire (10). Of these, the proximal end of the distal engaging element (90) can be fixed to the distal end (or tip) of the central wire (10) whereas the other three engaging elements (65 and 67) can freely slide on the central wire. Also, all the multiple engaging elements can be associated with the connection wire (190). In some embodiments, the flexible connection wire (190) can link proximal ends of all engaging elements at pre-set or equal space there between. In such embodiments, the engaging elements are fixed at their respective positions on the connection wire and maintain that distance with certain maneuvers. In addition, in some embodiments, the proximal end of the proximal engaging element (65) can be fixed to the distal end of the tubing compartment (27). The central wire can freely slide inside the tubing compartment. In certain embodiments, the device may further comprise or operably link to a handle (110) at the proximal end of the device, so that it can control (e.g. push or pull) the central wire.

FIG. 2 illustrates another embodiment of a method where a device comprising a plurality of engaging element such as that illustrated in FIG. 1 is used to remove or treat an occlusion/clot in a body lumen.

In some embodiments, the device can be introduced into blood vessel through a microcatheter (30). Upon arrival at the occluded site in the body lumen, and when pushing the device through microcatheter, the distal engaging element (90) may first be pushed forward with the central wire. Continued pushing force on the central wire will maintain the connection wire(s) under tension, and would pull each engaging element that is associated with the connection wire forward along the microcatheter lumen. In addition, continued forward pushing force while retracting the microcatheter would allow the operator to unsheathe the device and maintain a set distance between the engaging elements. Because the connection wire may be flexible, but is generally not stretchable, it allows the engaging elements to move closer to each other when it is slack, but prevents the engaging elements from being separated more than a preset distance when it is under tension. The engaging elements, upon being unsheathed from the microcatheter, will be positioned with the pre-set distance there between.

Upon unsheathing, the central wire (10) may be held stable so that the distal engaging element (90) that is fixed at the distal end of the central wire can be stabilized. The friction between the inner lumen of the microcatheter and the surface of the engaging elements (65 and 67) can cause the free sliding engaging elements move backward; however, because the connection wire is not stretchable, it holds the pre-set space between each elements. After unsheathing, the engaging elements may self-expand. An operator can adjust the spaces between the engaging elements. To engage or hold the clot, an operator may shorten the space between the engaging elements (i) by pulling the central wire backward (i.e. proximally) while holding the tubing compartment (27) stable, (ii) by pushing the tubing compartment forward (i.e. distally) while holding the central wire stable or (iii) by pulling the central wire backward and pushing the tubing compartment forward. This adjustment of the position of the engaging elements and the space there between will allow at least part of the clot to be compressed/cinched or caught in the space gap. See, e.g. FIGS. 2 B, C. Alternatively or in combination, the occlusion can be immobilized via the frictional engagement with the body lumen and one or more engaging element(s). The occlusion can also be directly engaged with the wires or struts of the engaging elements. Also, the occlusion can be immobilized and captured between one or more engaging element(s) and the body lumen. See, also, e.g. FIGS. 2 B and C. In some embodiments, the engagement (capture) and containment of the occlusion may involve more than one mode. Therefore, for example, at least part of the occlusion may be captured by direct engagement with one or more engaging elements and also at least some other part of the occlusion may be captured between the space(s) of two or more engaging elements. Also, alternatively or in combination, some part of the occlusion can be frictionally captured and immobilized by the body lumen and the engaging element(s).

In some embodiments, during the treatment procedure, while holding the tubing compartment, the central wire can be pulled proximally. The distal engaging element then may move backward and cinch or hold the clot with the adjacent engaging element(s). The proximal and/or its adjacent engaging elements are then pushed backward (i.e. proximally) by the compressed clot and this will in turn compress and cinch the occlusion. The operator can shorten the distance between the engaging elements until the occlusion is securely cinched/grabbed by the device. The modes of securely cinching/grabbing the occlusion may include one or more of the following: (1) the occlusion may be cinched or held between the engaging elements, (2) the occlusion may be directly engaged with the wires or struts of one or more engaging elements, (3) the occlusion may be frictionally contained between the body lumen and one or more of the engaging elements, and (4) the occlusion may be frictionally contained between the body lumen and the space(s) between the engaging elements, Once the occlusion is believed securely grabbed or cinched by the device, the device can then be pulled out of the body lumen. In some embodiments, e.g. those shown in FIG. 1B and FIG. 2C, the connection wire may be thin and flexible and thus it can bend, curl or bow once when the distance between the engaging elements are shortened.

Figure 3:
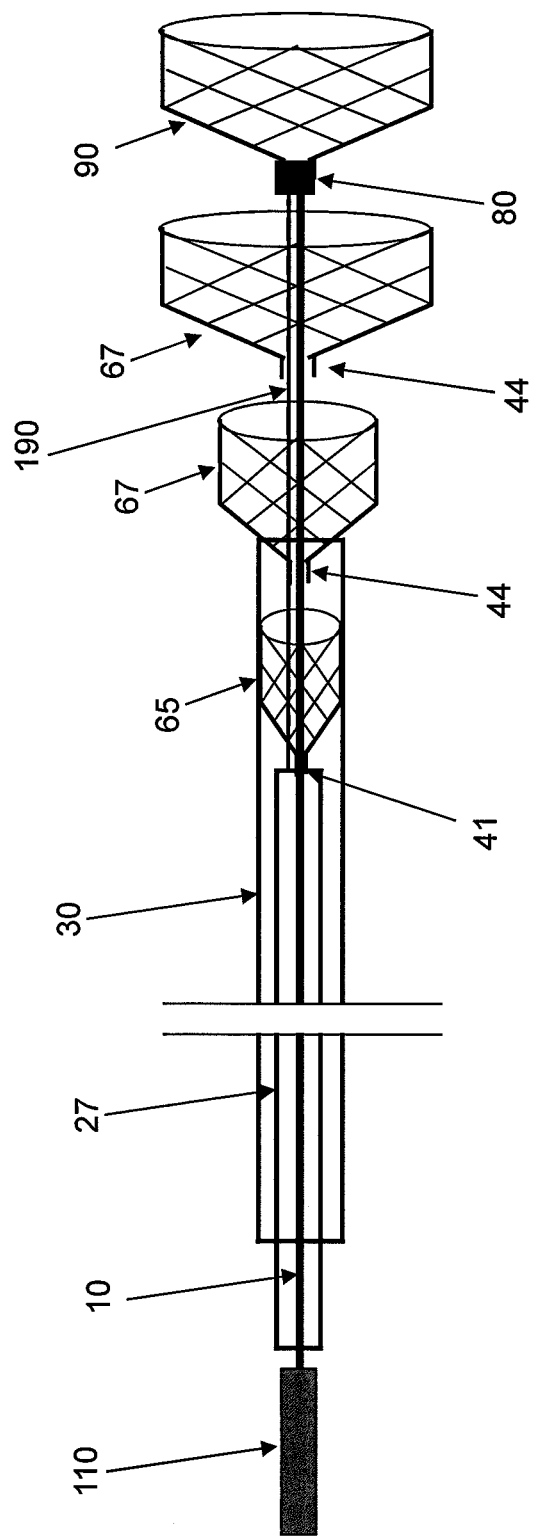
FIG. 3 shows still another non-limiting, illustrative example of a device according to some embodiments of the invention where the device comprises a plurality of engaging elements and a connection wire connecting the engaging elements. The device may be delivered through a microcatheter into the body lumen. This figure also shows that the device can be configured to be retrieved back to the microcatheter without elements overlapping each other.

FIG. 3 illustrates another embodiment of a device where the device may comprise a plurality of engaging elements. In some embodiments, when the device needs to be withdrawn into a microcatheter (30) during a retrieval procedure, the tubing compartment (27) can be pulled backward. The proximal engaging element (65) which is fixed to the tubing compartment can be pulled into the microcatheter (30). When the connection wire (190) is maintained under tension, it pulls the engaging elements that are connected to the connection wire into the microcatheter one by one. This retrieval mechanism allows the connection wire to extend to the pre-set distance between the engaging elements and prevents the plurality of engaging elements from stacking up on each other so that they can be pulled back into the microcatheter. The stacked up engaging elements may have too large a diameter to fit in the microcatheter and they may also be damaged when pulled into a position in which they are stacked up.

Figure 4:
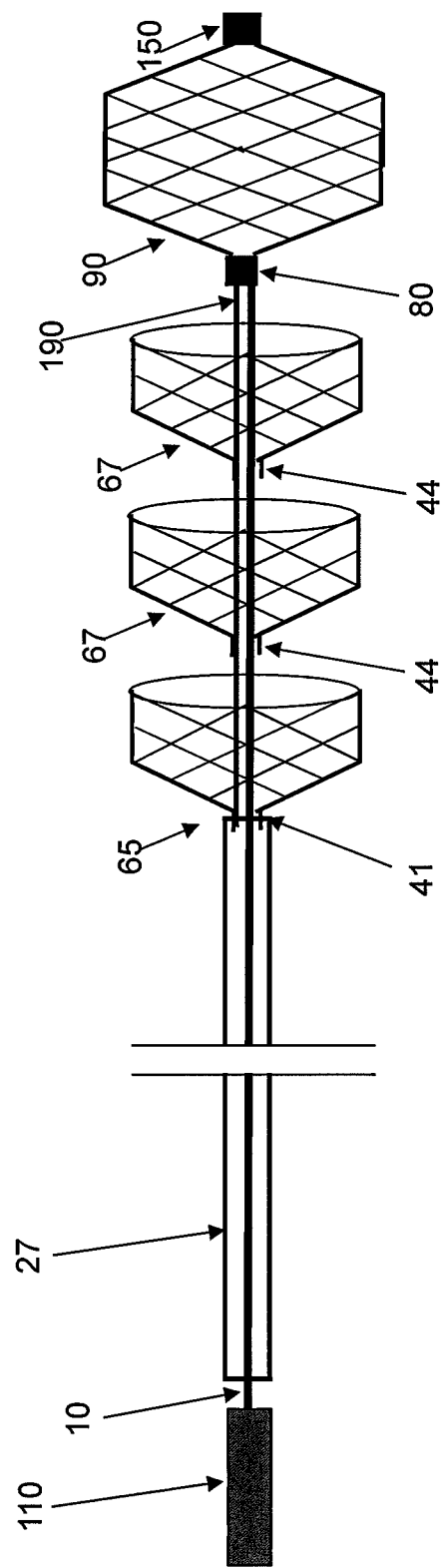
FIG. 4 shows still another non-limiting, illustrative example of a device according to some embodiments of the invention where the device comprises a plurality of engaging elements. In this particular embodiment, the distal engaging element of the device may have a closed end at its distal end. In addition, the distal engaging element may be larger in size (length and diameter) than the other engaging elements. However, the stiffness of the distal engaging element can be less than that of the other engaging elements to avoid vessel damage.

FIG. 4 illustrates still another embodiment of a device where the device may comprise a plurality of engaging elements. In some embodiments, the device may further comprise a distal engaging element (90) that also may function as distal filter. In certain embodiments, the distal end (or tip) of the distal engaging element can be closed by the distal connector (150). In some embodiments, the profile of the distal engaging element (90) can be larger in size (length and diameter) than that of other engaging elements and is less stiffer than the other engaging elements. This can minimize radial force of the distal engaging element against the vessel wall. This distal engaging element, especially in a distal filter form, can prevent clot debris from going downstream. If the clot (or occlusion) fragments during the treatment procedure, and generates debris, the debris can be caught (collected or contained) by this distal filter element (90). Since the profile of the distal engaging (filter) element is large, preferably slightly larger than the diameter of the vessel in the retrieval pass, the debris may not be able to escape between the engaging element and the wall of the vessel. In this embodiment the distal engaging element can also function to cinch or hold clot with the more proximal adjacent engaging element.

In addition, in certain embodiments, the proximal end or the distal end of the distal engaging element can be fixed to the central wire (10). Also, there can be a flexible connection wire (190) that links (associates or connects) the other engaging elements. In some of such embodiments, all the engaging elements are fixed at their respective positions on the connection wire (190), thereby setting spaces between each engaging element. In some embodiments, the proximal engaging element (65) can be fixed at about the distal end of the tubing compartment (27). With this configuration, when the tubing compartment (27) is pushed or pulled, the position of the proximal engaging element can also be adjusted. When the connection wire is under tension, the middle engaging elements can be pulled proximally by the tubing compartment, and pushed distally by the central wire)

In some other embodiments, all the engaging elements are associated with (or connected to) the central wire (10). In certain embodiments, only some (not all) engaging elements are fixed to the central wire whereas some others are able to move freely on the central wire. Therefore, for example, the distal engaging element (90) of FIG. 4 can be fixed at a position of the central wire whereas the proximal engaging element (65) and the middle/intermediate engaging elements (67) can freely slide on the central wire. With this configuration, the distal engaging element can be further controlled upon pushing or pulling the central wire via a handle (110) by an operator, and this can position the most distal extent of the device. Once the distal engaging element is positioned, the operator can further adjust the position of other engaging elements and the distance/space between the engaging elements by controlling the connection wire (190) via controlling the tubing compartment (27).

Figure 5:
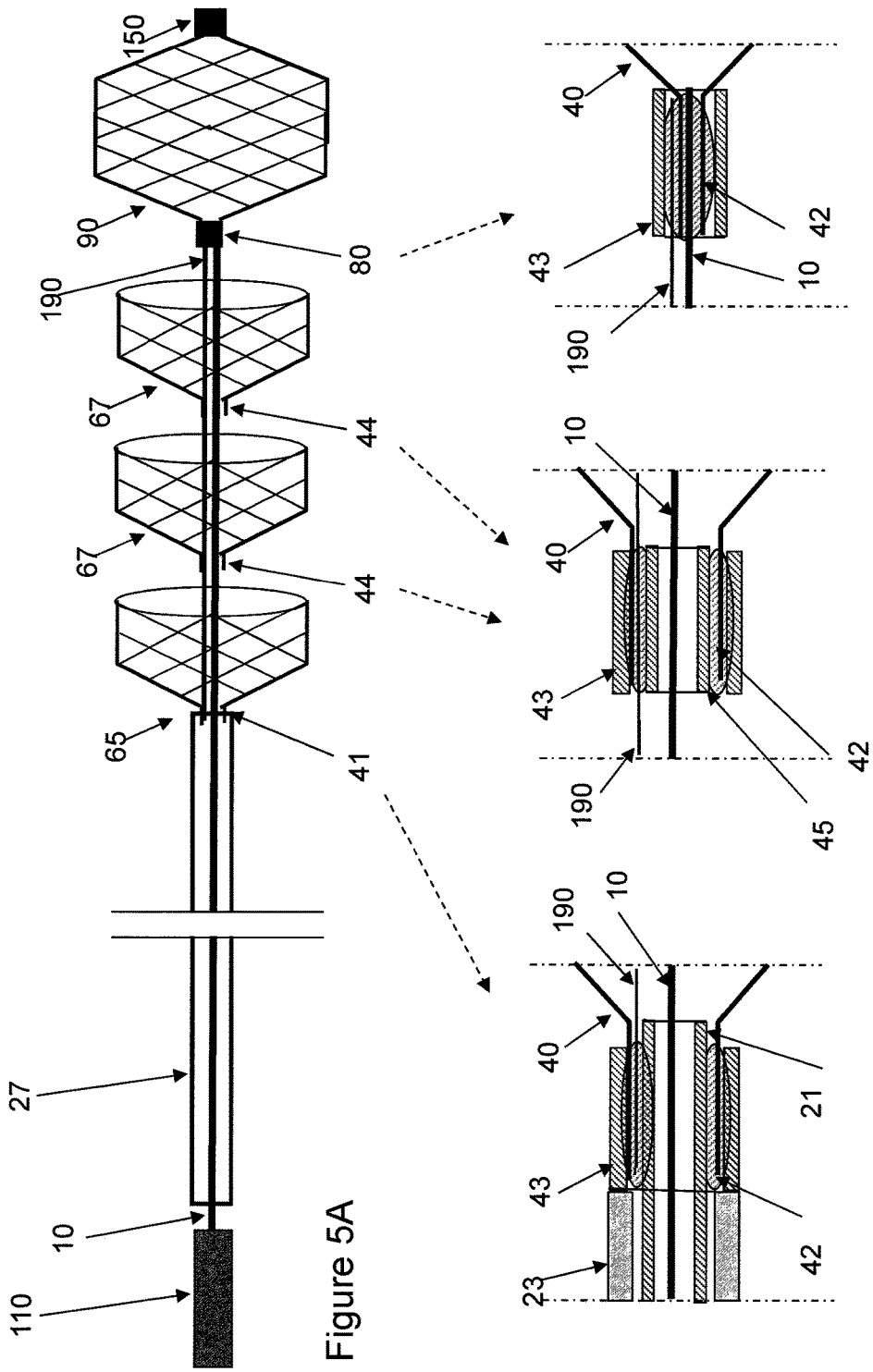
FIG. 5A shows still another non-limiting, illustrative example of a device according to some embodiments of the invention where the device comprises a plurality of engaging elements.
FIGS. 5B-D show detailed locations and structures of connectors at the proximal end of proximal engaging element, middle engaging elements, and distal engaging element.

FIG. 5A-D shows detailed structure, especially the connectors of the device according to some embodiments of the invention. FIG. 5B shows that the proximal engaging element is fixed to the distal end of the tubing compartment by a connector (41) which consists of an outer connector tubing (43) and an inner pusher tubing (21). The connection wire (190) and legs of the proximal engaging element (40) are fixed/bonded in between the wall of the two portions of tubing with joint media (42). Similarly, FIG. 5C shows the middle engaging element connector (44). The connection wire (190) and the legs of the middle engaging element (40) are fixed/bonded in between the wall of the two connector tubing portions with joint media (42). FIG. 5D shows the distal connector (80) joins the distal tip of the central wire (10), the connection wire (190), and the legs (40) of the distal engaging element (90) with a short outer connector tubing (43) filled with joint media (42). The central wire (10) passes the hollow space of the inner connectors (21 and 45), allowing the proximal and middle engaging elements (65, 67) sliding freely over the central wire.

Figure 6:
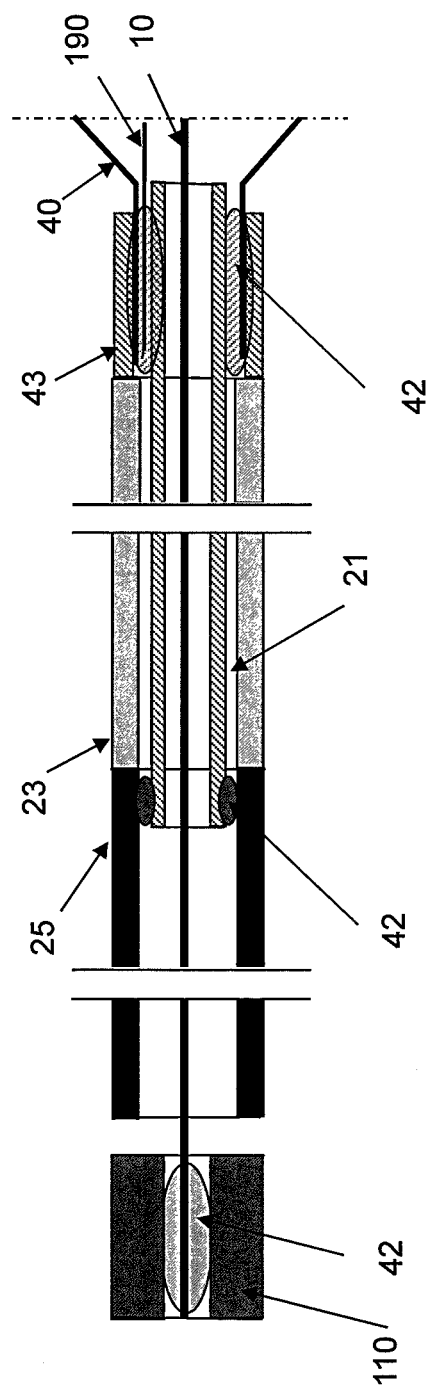
FIG. 6 shows still another non-limiting, illustrative example embodiment of a device according to some embodiments of the invention where the device comprises a plurality of engaging elements. A non-limiting structure and components of a tubing compartment, central wire handle, and connections among components are illustrated in this figure.

FIG. 6 shows a non-limiting, illustrative structure of a tubing compartment according to some embodiments of the invention. The tubing compartment may comprise or consist of three major components, the inner distal pusher tubing (21), the outer distal pusher tubing (23) and the proximal pusher tubing (25). All are bonded/connected by joint media (42). This figure also shows that the proximal end of the central wire is jointed to a handle (110) by joint media (42). The distal pusher tubing (21, 23) is generally flexible so that the device can pass tortuous segment of a vessel. The proximal pusher tubing (25) is stiff to ensure the device can be pushed through microcatheter.

FIG. 7A-C illustrates still another embodiment of a device where the device may comprise a plurality of engaging elements. In some embodiments, the device may comprise a central wire (10), a control wire (100), and a plurality of self-expandable engaging elements, each of which can be about 2 to about 25 mm long or longer longitudinally. The length of the individual engaging elements when expanded, which can be identical, similar or different from each other, can be about 1 mm, about 2 mm, about 4 mm, about 5 mm, about 6 mm, about 7 mm, about 8 mm, about 9 mm, about 11 mm, about 12 mm, about 13 mm, about 14 mm, about 15 mm, about 16 mm, about 17 mm, about 18 mm, about 19 mm, about 20 mm, 21 mm, 22 mm, 23 mm, 24 mm, and 25 mm, In some embodiments, the length of the individual engaging elements when expanded, which can be identical, similar or different from each other, can be about 25 mm or longer.

The proximal end of the distal engaging element (90) can be fixed at about the distal end of the central wire (10), the structure of the connection is the same as that already illustrated in FIG. 5D. The proximal end of the proximal engaging element (65) and the connection wire (190) can be fixed at about the distal end of the control wire (100) by the proximal end connector (41) consisting of an outer connection tubing (43), an inner connection tubing (45) and joint media (42) as shown in FIG. 7B. The middle/engaging elements are fixed to the connection wire (190) through connector 44 as shown in FIG. 7C, the structure of the connection is the same as and already described previously in FIG. 5C. The proximal connector (41) and the middle connector (44) can freely slide on the central wire (10). In some embodiments, a thin flexible connection wire (190) links the proximal ends of all engaging elements with a pre-set or equal space/distance between each adjacent element. In certain embodiments, the distal segment of the control wire can be tapered down into a thin more flexible section and serve as connection wire. In such case, the proximal end of the proximal engaging element can be directly joined to the control wire where the thin section starts, as shown in FIG. 7C (i.e. the connection wire 190 is a segment/part of the control wire 100). The control wire (100) may have a handle (120) attached at the proximal end of the device. The central wire can freely slide inside the handle tube and the connector at the tip of the control wire, as well as the middle connectors. In addition, the device can have a separate handle 110) that can control the movement of the central wire.

In some embodiments, all the engaging elements are fixed at their respective positions on the connection wire (100), thereby setting a pre-set space/distance there between. On the other hand, while all the engaging elements can be associated with (or connected to) the central wire (10), only the distal engaging element (90) may be fixed at the central wire (10) and the other engaging elements may be able to freely move along the central wire. In some of such embodiments, upon controlling one or both of the central wire and control wire, the position of each the distal and proximal engaging element and the space there between can be adjusted in order to securely cinch or grab an occlusion/clot.

FIGS. 8A-F illustrate still another embodiment of a device where the device may comprise a plurality of engaging elements. In some embodiments, the device may comprise a plurality of engaging elements some of which may form an engaging (or operation) unit/pair. The receiving element is connected with the spacing wire (191), which may be stiffer than the connection wire (190) describe previously. The spacing wire will not be as flexible or soft so that it cannot fold/bend under compression and therefore remains elongated. FIG. 8A shows the distance in between the receiving and capturing engaging elements is being fully opened and FIG. 8B shows the space is shortened. FIG. 8D, 8E, 8F shows the detailed structure of the proximal receiving engaging element connector (41), the middle capturing engaging element connector (44), and the distal capturing engaging element connector (80), respectively. In some embodiments, the device may comprise a central wire (10), a tubing compartment (27), and a plurality of operation unit/pair. In some embodiments, the device may comprise two or more pairs of clot cinching self-expandable engaging elements (each pair comprising 68 and 69 is considered as one operation unit/pair). In each operation unit/pair, there can be at least two or more engaging elements, at least one being a receiving element (e.g. a proximal, receiving element and a middle receiving element (68)), and at least another being a capturing element (e.g. a middle, capturing element and a distal capturing element (69)).

In certain embodiments, the capturing element may comprise a plurality of wires or struts that can directly engage with an occlusion. Alternatively or in combination, the capturing element can cinch or grab the occlusion via the frictional engagement with a body lumen and/or within the space between the capturing element and the other engaging (receiving or capturing) element. The capturing element, in at least some embodiments, has a closed end at its proximal end. The open end of the catching elements can either face distal or proximal side of the device. In some embodiments, all of the capturing elements (from different operation units/pairs) can be fixed to the central wire (10) via connectors (47, 80) and the receiving elements are fixed to a spacing wire (191) via connectors (41, 44) while the capturing elements may not be connected to the spacing wire. The receiving element can be located proximal to the capturing element and may be shaped in a manner that conforms to the shape of the capturing element which is distal to it. Therefore, in some embodiments, the proximal portion of a capturing element can fit within the distal portion of its proximally located receiving element In certain embodiments, the most proximally located receiving element (68) may be fixed to the distal end of the tubing compartment (27). In addition, all receiving elements can also be fixed at their respective positions of the spacing wire (191). Thus, the spacing wire may connect all the receiving elements (68), keeping the distance between receiving elements. Therefore, in such a configuration, by controlling the tubing compartment, the position of all the receiving elements can also be controlled while maintaining the distance there between due to the pre-set distance set by the association with the spacing wire.

In some embodiments, some or all of the capturing elements (from different operation units/pairs can be fixed to the central wire (10). The central wire can freely slide inside the tubing compartment (27) as well as inside the connectors of the receiving engaging elements. With this configuration, the position of all the capturing elements can be controlled via the movement of the central wire.

Accordingly, in some embodiments, the position of the engaging elements can be controlled by the movement of the central wire and/or the tubing compartment. For example, the spaces between the receiving elements and capturing elements can be controlled by sliding the central wire in the tubing compartment. Alternatively or in combination, the pushing or pulling of the tubing compartment can also result in lengthening or shortening the distance between the receiving elements and capturing elements.

FIG. 9 illustrates still another non-limiting embodiment of a method according to the invention where the device illustrated in FIG. 8 is used to treat or remove one or more occlusion(s) from a body lumen.

In some embodiments, the device may be introduced through a microcatheter (30), by pushing the central wire (10) and the tubing compartment (27). See FIGS. 9A and D. The spacing wire (191) can maintain spaces between the receiving elements (68). The catching elements (69) can all be fixed to the central wire (10). Upon unsheathing (see FIGS. 9B and E), the engaging elements may expand and foreshorten increasing the distance between the operation units/pairs and also between the individual engaging elements. The distance between engaging elements as well as different operation units/pairs will allow an occlusion (clot) to lodge in the space gaps. While holding the tubing compartment (27) stable and pulling the central wire proximally (see FIGS. 9C and F), the catching elements (69) are moved backward. The spaces between the catching and receiving elements are all shortened and part(s) of the occlusion lodged in the spaces between the engaging elements are cinched/grabbed or held. The device can then be pulled out from the body lumen (e.g. a blood vessel).

Figures 9A, 9B, 9C:
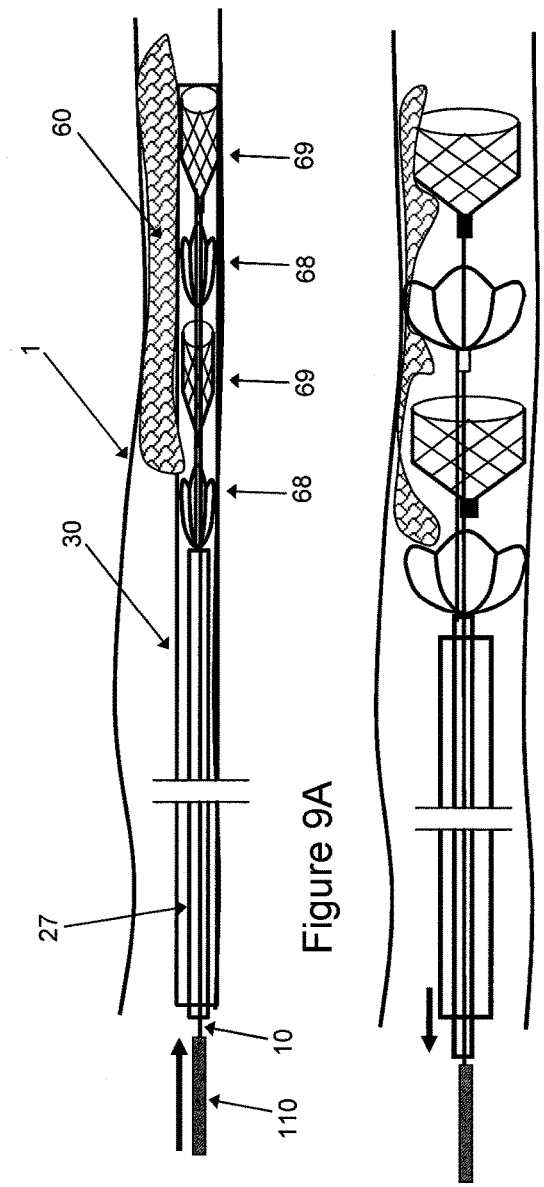
FIGS. 9A-F show still another non-limiting embodiment of a method according to the invention where the device illustrated in FIG. 8 is used to treat or remove one or more occlusion(s) from a body lumen.
Figure 9D:
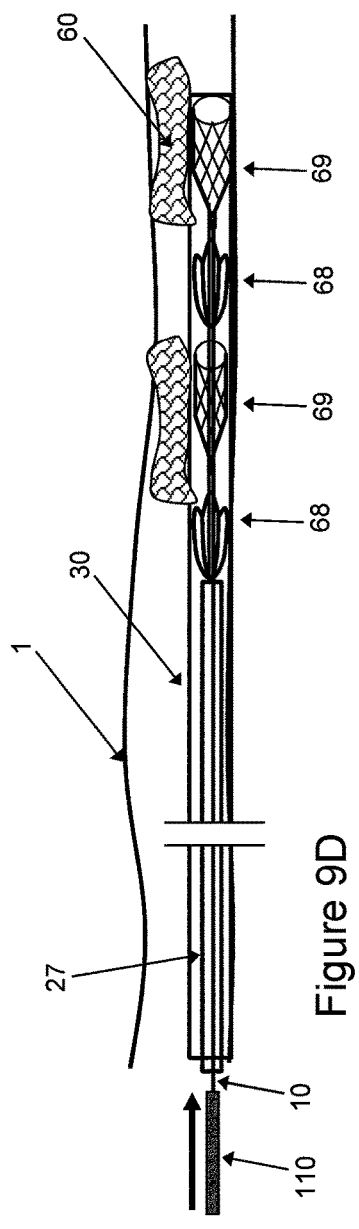
Figure 9E:
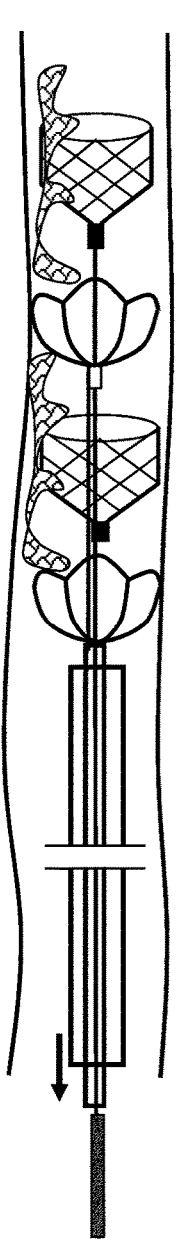
Figure 9F:
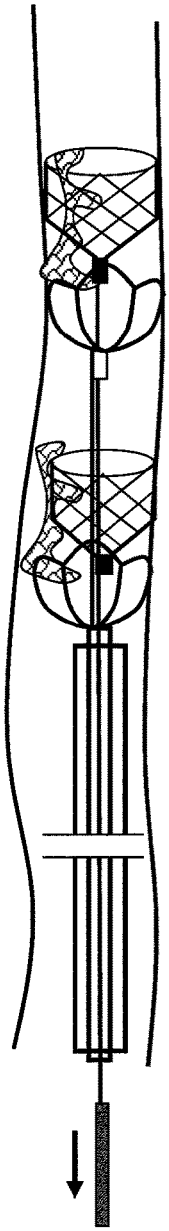

In certain embodiments, e.g. as shown in FIGS. 9A-C, a relatively large or long length of occlusion can be treated or removed by the device comprising a plurality of operation units/pairs. In some of such occasions, more than one operation unit/pair can involve cooperatively to cinch and grab the occlusion. Alternatively or in combination, more than one occlusion can be individually treated or removed by a separate operation unit/pair as illustrated in FIGS. 9D-F. Already explained elsewhere in the application, the mechanism of cinching or grabbing (engaging, capturing or containing) the occlusion by the device can be various, e.g. (1) the occlusion may be captured within the spaces between the engaging elements, (2) the occlusion may be directly engaged with the wires or struts of one or more engaging elements, (3) the occlusion may be frictionally contained between the body lumen and one or more of the engaging elements, and (4) the occlusion may be frictionally contained between the body lumen and the space(s) between the engaging elements.

Figure 10:
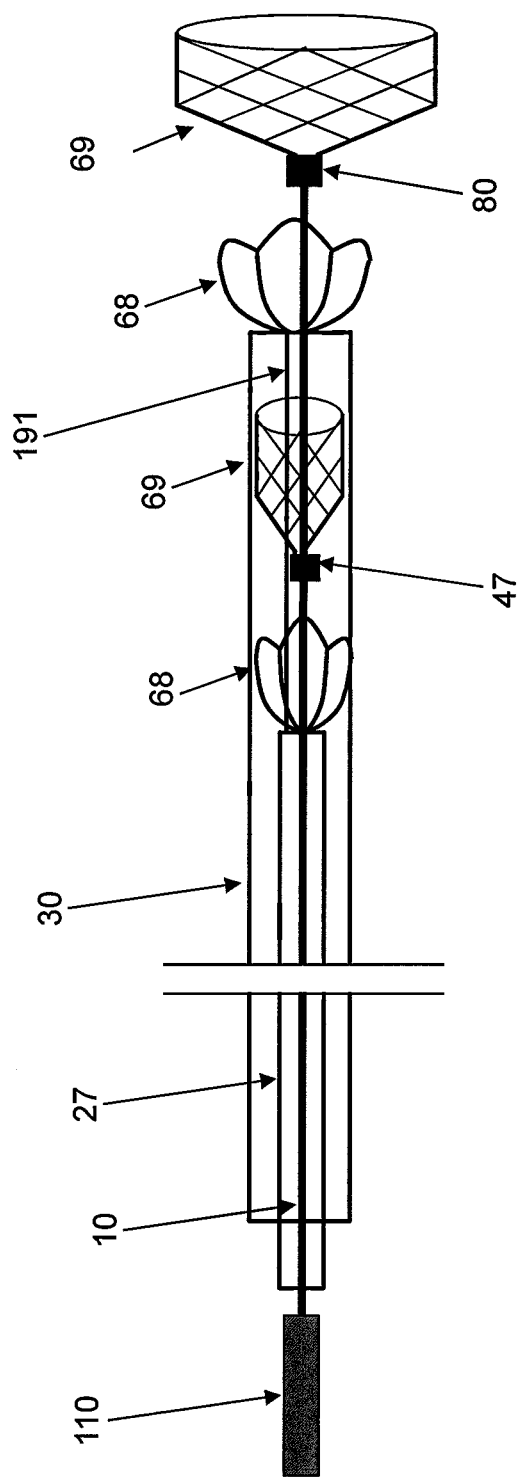
FIG. 10 shows still another non-limiting embodiment of a device according to the invention where the device comprises a plurality of engaging elements, some of which may function as a receiving element whereas some other of which may function as a capturing/cinching element. This figure shows the engaging elements are pulled back into a microcatheter when there is a need during operation.

FIG. 10 illustrates still another embodiment of a device where the device may comprise a plurality of engaging elements. In some embodiments, when the device needs to be withdrawn back into a microcatheter (30) during a retrieval procedure, the tubing compartment (27) can be pulled backward, allowing the spaces between receiving elements and catching elements to increase to prevent them from stacking up on top of each other. Thus all engaging elements can be pulled into the microcatheter.

Figure 11A:
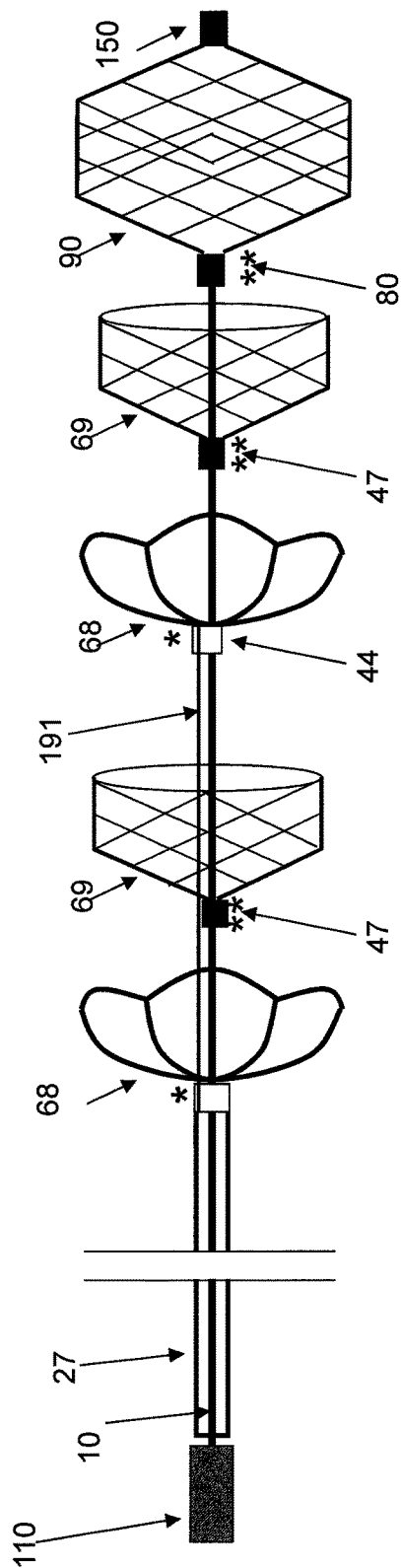
FIGS. 11A-B show still another non-limiting embodiment of a device according to the invention where the device comprises a plurality of engaging elements, some of which may function as a receiving element whereas some other of which may function as a capturing element. In certain embodiments, a separate distal engaging element may be added at the tip of the central wire to catch the clot debris which may be closed at its distal end. Further, in some embodiments, the distal engaging element may be larger in size and diameter than the other engaging elements. However, the stiffness of the distal engaging element can be less than that of the other engaging elements.
Figure 11B:
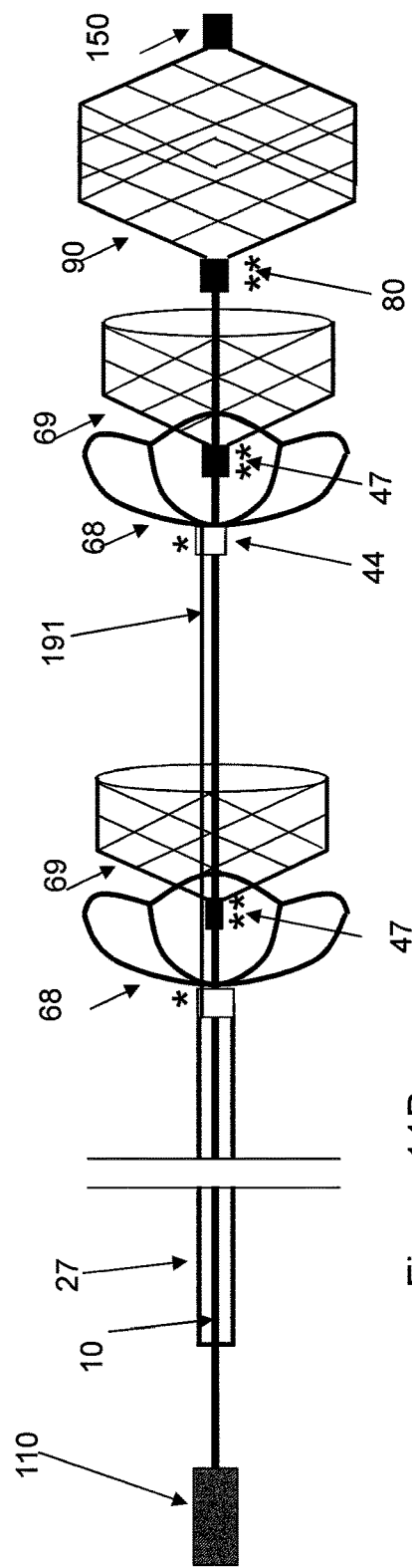

FIGS. 11 A and B illustrate still another embodiment of a device where the device may comprise a plurality of engaging elements. As an alternative design of the device, in addition to a plurality of operation unit/pair, the device may further comprise an additional element (90) at the distal end of the device. This additional element may function as a distal filter. In certain embodiments, the distal end of the distal filter element can be closed by a distal connector (150) to more efficiently capture the clot debris. In some embodiments, the profile of the distal filter element (90) in size and diameter can be larger than that of other engaging elements and is less stiff than the other engaging elements. This can minimize radial force of the distal filter element against the vessel wall. This most distal engaging element (90) can serve to both cinching/grabbing the clot or occlusion and act to catch or filter clot debris. Therefore if the clot (or occlusion) breaks down during retrieval procedure, and generates a plurality of debris, the debris can be caught (collected or contained) in this distal filter element. Since the profile of the distal engaging (filter) element is large, preferably larger than the diameter of the vessel the debris may not be able to escape between the engaging element and the wall of the vessel. In FIG. 11, "*" represents where the capturing elements (69) may be fixed to the central wire (10) and "*" represents where the receiving elements (68) may be fixed to the spacing wire (191) in some embodiments.

FIG. 12 illustrates still another embodiment of a device where the device may comprise a plurality of engaging elements. In some embodiments, the device may comprise a central wire (10), a control wire (100), and a plurality of operation unit/pair, e.g. each unit/pair comprising two, or more pairs of clot engagement elements. In each of the engagement operation unit/pair, at least one receiving element and one capturing element may be present, and generally the receiving element may be located proximal to the capturing elements. In some embodiments, some or all of the (proximal and intermediate) receiving elements (68) may be fixed to the control wire (100). In some other embodiments, the (distal and middle) capturing elements (69), can be fixed to the central wire (10) via connector (47, 80). In certain embodiments, the proximal and middle receiving element (68) can be associated with (or connected to) the central wire (10) but freely slide on the central wire.

In certain embodiments, the control wire (100) may have a handle (120, e.g. a type of tube) attached at the proximal end of the control wire, and the central wire can freely slide inside the handle tube lumen. In addition, the central wire (10) may also be operably linked to a handle (110). Therefore, by controlling one or both of the control wire and the central wire, the space between the engaging elements can be adjusted so as to maximize the engagement and containment of an occlusion by the device.

FIGS. 12A and B show the adjustment of the distance between the engaging elements. For example, in the embodiment of FIG. 12B, while holding the control wire handle and pulling the central wire (10) proximally, the capturing elements (69) will move backward, shortening the distance between their receiving elements. When pulling the central wire back (i.e. proximally), the distance between the catching and receiving element will shorten, cinching or grabbing the clot at various points. As apparent from the illustration, e.g. conversely, by pushing the control wire distally, the receiving elements will move forward (distally), thereby the distance between the engaging elements will shorten. Therefore, by controlling the movements of the central wire (10) and/or the control wire (100), the position of both the capturing and receiving elements can be adjusted, thereby increasing or shortening the space between the engaging elements.

FIGS. 12C to E show certain, non-limiting embodiments of a connector such as (41) and (44) where the engaging element, especially a receiving element, is configured to move along the central wire but fixed to the control wire. In certain embodiments, a short outer connector tubing (43) and a short inner connection tubing (45), as well as joint media (42) can be used to join the control wire (100), the legs of the distal receiving element (40). The central wire can freely slide inside the inner connector tube (45). All capturing elements are fixed to the central wire via connector (47, 80)

The control wire and spacing wire can be from the same wire, which may be tapered down at the distal segment that serves as a spacing wire to ensure enough flexibility of the engagement compartment. Therefore, in some embodiments, as shown in FIG. 12E, the control wire (100) functions as a spacing wire (190) in the distal portion of the device.

FIGS. 13A-F illustrate still alternative embodiments of a device where the device may comprise a plurality of operation unit/pair. In some embodiments, all receiving elements (68) are free-sliding on the central wire (10) and all catching elements (69) are fixed to the central wire via connectors (47, 80), forming multiple pairs of cinching units/pairs. In each of the engaging operation units/pairs, at least one receiving element and one capturing elements may be present, and generally the receiving element may be located proximal to the capturing elements. In some embodiments, a relatively thick or more rigid, spacing wire (191) may connect all receiving elements (68) to maintain the space between them. Each unit/pair of capturing element (69) and receiving element (68) can be connected to a connection wire (190). All receiving elements can freely slide on the central wire (10). As shown in FIG. 13D, the proximal connector (41) connects a spacing wire (191), a connection wire (190) and the legs (40) of proximal engaging element in between an outer and inner connection tubes filled with joint media (42). FIG. 13E shows the detailed structure of the receiving engaging element connector (44). It connects a connection wire (190) and the legs (40) of a receiving engaging element in between an outer connection tube (43) and an inner connection tube (45) filled with joint media (42). FIG. 13F shows a similar structure of connector (44) connecting a spacing wire (191), a connection wire (190), and the legs of receiving engaging element in between an outer connector tube (43) and an inner connection tube (45) filled with joint media (42). The central wire can slide freely inside the inner connectors (45). In such embodiments, the capturing elements (69) may be fixed to the central wire via connectors (47 and 80) and the connection wire (190). All the receiving elements are fixed to the spacing wire via connectors (41 and 44).

In addition, the connection wires (191) link each pair of capturing and receiving elements in a same engaging/operation unit/pair to maintain the pre-set space between the paired engaging elements, especially when introducing device through a microcatheter (30). After unsheathing, and pulling the central wire backward, the distance between the receiving and capturing elements can be reduced and an occlusion (clot) can be cinched, grabbed or held in between the engaging elements. When pulling back the device into the microcatheter, the connection wires (190) buckle; elements of each pair may overlap, however, the profile, or the struts of the distal end of the catching element as well as the receiving element can be designed to be small. Therefore if the two engaging elements stack up, they will still be smaller than the diameter of the microcatheter. Thus the device can be retrieved back into the microcatheter. In certain embodiments, the microcatheter can serve as a stopper of all the receiving elements when catching the occlusion (clot) by pulling back the central wire and the catching elements. The advantage of this design is that there is only one handle at the proximal end of the device. An operator only needs to pull the central wire back to shorten the spaces between the receiving and catching elements to cinch a clot. The position of the engaging element will be self-adjusted and clot will be engaged and held.

FIGS. 14 A-E shows non-limiting structures of the engaging element. Alternatively the engagement can be in the form/shape of, but not limited to, conical (FIG. 14A), sphere (FIG. 14D), ellipsoid (FIG. 14D), parachute (FIG. 14E), cylinder (FIG. 14C), or any combination of above structures (e.g. as shown in FIG. 14B). The cylindrical form may also be closed or open at either the distal or proximal ends.

FIGS. 15A-B show alternative, non-limiting illustrative embodiments of structures that may form into engaging elements. The engaging elements may have proximal legs (40) and actual engaging element struts (50). The device according to some embodiments of the invention can be manufactured by a variety of techniques that are known in the art. For example, the engaging element/struts can be fabricated from a thin sheet by laser cutting or photo etching process. Alternatively, the engaging elements can also be fabricated from a piece of hypo tube material by laser-cutting. The struts shown in FIG. 15 or laser cut hypo-tube may be heat set into a desired shape and size of the engaging element and further chemically polished or electro-polished. The component can be assembled into a retrieval device described in this article.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device for use in a body lumen comprising:
a central wire comprising a proximal end and a distal end thereof;
a plurality of engaging elements comprising a distal engaging element, a proximal engaging element, and one or more middle engaging elements, each of the plurality of the engaging elements being associated with the central wire;
   wherein each of the plurality of engaging elements comprises a distal end and a proximal end thereof;
   wherein the distal engaging element is most distally located among the plurality of the engaging elements and is fixed to a distal tip of the central wire;
   wherein the proximal engaging element is most proximally located among the plurality of the engaging elements and can freely slide on the central wire; and
   wherein the one or more middle engaging elements is located between the distal and proximal engaging elements and can freely slide on the central wire, each of the one or more middle engaging elements having an open distal end;
a flexible connection wire that associates with the proximal engaging element and at least one more engaging element of the plurality of engaging elements, said flexible connection wire configured to set the associated engaging elements apart at a pre-set distance; and
a proximal end control element that is located proximal to the proximal engaging element, wherein the proximal end of the proximal engaging element is fixed at the proximal end control element;
wherein the device has an open state including spaces between each adjacent engaging element that are open the pre-set distance and a closed state including spaces between each adjacent engaging element shortened from the pre-set distance to a second distance; and
wherein pulling the control element proximally while holding the central wire causes the distance between the capture elements to increase until the connection wire is under tension, thereby setting the associated engaging elements apart at the pre-set distance.

2. The device according to claim 1, wherein the proximal end control element comprises a tubing compartment comprising a distal end and a proximal end thereof, and the proximal end of the proximal engaging element is fixed at about the distal end of the tubing compartment.

3. The device according to claim 2, wherein the central wire can freely slide inside the tubing compartment.

4. The device according to claim 1, wherein the proximal end control element comprises a control wire comprising a distal end and a proximal end thereof, and the proximal end of the proximal engaging element is fixed at about the distal end of the control wire.

5. The device according to claim 1, wherein the proximal end control element comprises a wire comprising a distal end and a proximal end thereof, a distal segment of the wire is flexible serving as a connection wire, and all of the engaging elements are fixed to the connection wire.

6. The device according to claim 1, wherein at least one of the plurality of engaging elements comprises a plurality of wires or struts.

7. The device according to claim 1, wherein at least one of the plurality of engaging elements is self-expandable.

8. The device according to claim 1, wherein an overall shape of the engaging elements is conical, spherical, tubular, ellipsoid, or any combination thereof.

9. The device according to claim 1, wherein the pre-set distance between the associated engaging elements is an equal distance.

10. The device according to claim 1, wherein the flexible connection wire is flexible or floppy to allow the pre-set distance between the free-sliding engaging elements to be shortened when it is desired to bring the engaging elements closer together.

11. The device according to claim 1, wherein one or more of the engaging elements are linked with a spacing wire which is stiffer than the connection wire to maintain spaces between each adjacent engaging element the distance at the open state.

12. The device according to claim 1, wherein the proximal end of the central wire is operably linked to a handle to allow controlling the distal engaging element upon pushing or pulling the central wire.

13. The device according to claim 1, wherein the pre-set distance between the engaging elements may be adjusted 0 mm, 5 mm, 10 mm, 15 mm, 20 mm, 25 mm, 30 mm, 35 mm, 40 mm, 45 mm, and 50 mm, or any range therebetween.

14. The device according to claim 1, wherein the closed state is configured to hold, cinch, or grab an occlusion or clot.

15. The device according to claim 1, wherein the distal engaging element has a closed distal end.

16. A method of removing at least part of an occlusion from a first location in a body lumen comprising:
   introducing the device according to claim 1 into the body lumen;
   locating the device at about the first location;
   engaging at least part of the occlusion with at least one of the plurality of the engaging elements; and
   removing the engaged occlusion from the first location.

17. The method according to claim 16, wherein said engaging comprises:
   adjusting the position of one or more of the plurality of the engaging elements by:
   holding the proximal end control element while pulling the central wire to engage the occlusion between at least two engaging elements, and/or
   holding the central wire while pushing the proximal end control element to engage the occlusion between at least two of the engaging elements.

* * * * *